(12) United States Patent
Whitehouse et al.

(10) Patent No.: US 8,487,243 B2
(45) Date of Patent: Jul. 16, 2013

(54) SAMPLE COMPONENT TRAPPING, RELEASE, AND SEPARATION WITH MEMBRANE ASSEMBLIES INTERFACED TO ELECTROSPRAY MASS SPECTROMETRY

(75) Inventors: Craig M. Whitehouse, Branford, CT (US); Thomas P. White, Clinton, CT (US)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 13/006,934

(22) Filed: Jan. 14, 2011

(65) Prior Publication Data

US 2011/0220789 A1    Sep. 15, 2011

Related U.S. Application Data

(63) Continuation of application No. 11/895,494, filed on Aug. 24, 2007, now Pat. No. 7,872,225, which is a continuation-in-part of application No. 11/803,984, filed on May 15, 2007, now Pat. No. 7,619,216, which is a continuation of application No. 11/132,953, filed on May 19, 2005, now Pat. No. 7,232,992.

(60) Provisional application No. 60/840,095, filed on Aug. 25, 2006.

(51) Int. Cl.
*B01D 59/44* (2006.01)
*G01N 24/00* (2006.01)

(52) U.S. Cl.
USPC .......................... 250/288; 436/173; 436/140

(58) Field of Classification Search
USPC .......................... 250/288, 281, 282; 204/451
See application file for complete search history.

(56) References Cited

U.S. PATENT DOCUMENTS 4,542,293 A    9/1985    Fenn et al.
5,045,204 A    9/1991    Dasgupta et al.
(Continued)

FOREIGN PATENT DOCUMENTS

EP    0032770    7/1981
EP    0069285    1/1983
(Continued)

OTHER PUBLICATIONS

Provisional application 60/573,666, filed May 21, 2004.
(Continued)

*Primary Examiner* — Nikita Wells
*Assistant Examiner* — Johnnie L Smith
(74) *Attorney, Agent, or Firm* — Fish & Richardson P.C.

(57) ABSTRACT

The invention provides a method and apparatus for trapping, releasing and/or separating sample components in solution passing through a channel with or without packing material present by passing ion current through the channel driven by an electric field. A portion of the ion current comprises cation and/or anion species generated from second solution flows separated from the sample solution flow path by semipermeable membranes. Cation and/or Anion ion species generated in the second solution flow regions are transferred into the sample solution flow path through ion selective semipermeable membranes. Ion current moving along the sample solution flow path is controlled by varying the composition of the second solutions and/or changing the voltage between membrane sections for a given sample solution composition. The sample composition may also be varied separately or in parallel to enhance trapping, release and/or separation efficiency and range. The invention when interfaced to an Atmospheric Pressure Ion Source, that may include Electrospray Ionization, with mass spectrometric analysis enables independent control of the on-line sample separation process and the Atmospheric Pressure Ion Source or Electrospray ionization processes.

28 Claims, 16 Drawing Sheets

U.S. PATENT DOCUMENTS

| | | | |
|---|---|---|---|
| 5,306,412 | A | 4/1994 | Whitehouse et al. |
| 5,393,975 | A | 2/1995 | Hail et al. |
| 5,869,832 | A | 2/1999 | Wang et al. |
| 5,879,949 | A | 3/1999 | Cole et al. |
| 5,917,184 | A | 6/1999 | Carson et al. |
| 6,252,225 | B1 | 6/2001 | Takada et al. |
| 6,326,616 | B1 | 12/2001 | Andrien et al. |
| 6,437,327 | B2 | 8/2002 | Takada et al. |
| 6,501,073 | B1 | 12/2002 | Mylchreest et al. |
| 6,630,664 | B1 | 10/2003 | Syage et al. |
| 6,677,593 | B1 | 1/2004 | Van Berkel |
| 6,685,809 | B1 | 2/2004 | Jacobson et al. |
| 6,784,439 | B2 | 8/2004 | Van Berkel |
| 6,858,841 | B2 | 2/2005 | Truche et al. |
| 7,232,992 | B2 | 6/2007 | Whitehouse et al. |
| 7,619,216 | B1 | 11/2009 | Whitehouse et al. |
| 7,872,225 | B2 | 1/2011 | Whitehouse et al. |
| 2003/0209005 | A1 | 11/2003 | Fenn |
| 2005/0051485 | A1 | 3/2005 | Saini |
| 2005/0258360 | A1 | 11/2005 | Whitehouse et al. |
| 2005/0284762 | A1 | 12/2005 | Astorga-Wells et al. |
| 2006/0022130 | A1 | 2/2006 | Bousse et al. |
| 2006/0060769 | A1 | 3/2006 | Bousse et al. |
| 2008/0035484 | A1 | 2/2008 | Wu et al. |
| 2008/0264792 | A1 | 10/2008 | Moon et al. |
| 2009/0008547 | A1 | 1/2009 | Whitehouse et al. |
| 2009/0095899 | A1 | 4/2009 | Whitehouse et al. |
| 2009/0095900 | A1 | 4/2009 | Whitehouse et al. |

FOREIGN PATENT DOCUMENTS

| | | |
|---|---|---|
| EP | 0180321 | 5/1986 |
| EP | 0075371 | 3/1993 |
| JP | 2005/134168 | 5/2005 |
| WO | 02/80222 | 10/2002 |
| WO | 2006/062471 | 6/2006 |

OTHER PUBLICATIONS

Astorga-Wells, "A Microfluidic Electrocapture Device in Sample Preparation for Protein Analysis by MALDI Mass Spectrometry," Anal. Chem., 75(19):5213-5219, 2003.

Jackson and Enke, "Electrical Equivalence of Electrospray Ionization with Conducting and Nonconducting Needles," Anal. Chem., 71:3777-3784, 1999.

Kebarle, "A brief overview of the present status of the mechanisms involved in electrospray mass spectrometry," J. Mass. Spectrom., 35:804-817, 2000.

Kebarle and Ho, "On the Mechanism of Electrospray Mass Spectrometry," Chapter 1—Electrospray Ionization Mass Spectrometry—Fundamentals, Instrumentation, and Applications, Edited by Richard Cole, 3-63, 1997.

Kebarle and Tang, "From Ions in Solution to Ions in the Gas Phase—The Mechanism of Electrospray Mass Spectrometry," Anal. Chem., 65(22):972A-985A, 1993.

Kostiainen and Bruins, "Effect of Multiple Sprayers on Dynamic Range and Flow Rate Limitations in Electrospray and Ionspray Mass Spectrometry," Rapid Comm. In Mass Spec., 8:549-558, 1994.

Larminie and Dicks, "Proton Exchange Membrane Fuel Cells," Chapter 4—Fuel Cell Systems Explained, John Wiley and Sons, 67-119, 2003.

Park et al., "Concentration of DNA in a Flowing Stream for High-Sensitivity Capillary Electrophoresis," Anal. Chem., 75:4467-4474, 2003.

Severs et al., "Characterization of the Microdialysis Junction Interface for Capillary Electrophoresis/Microelectrospray Ionization Mass Spectrometry," Anal. Chem. 69:2154-2158, 1997.

Severs et al., "A New High-performance Interface for Capillary Electrophoresis/Electrospray Ionization Mass Spectrometry," Rapid Comm. in Mass Spec., 10:1175-1178, 1996.

Van Berkel, "The Electrolytic Nature of Electrospray," Chapter 2—Electrospray Ionization Mass Spectrometry- Fundamentals, Instrumentation, and Applications, Edited by Richard Cole, 65-105, 1997.

Van Berkel, "Insights into Analyte Electrolysis in an Electrospray Emitter from Chronopotentiometry Experiments and Mass Transport Calculations," J. Am. Soc. Mass Spec., 11:951-960, 2000.

Van Berkel et al., "Enhanced Study and Control of Analyte Oxidation in Electrospray Using a Thin-Channel, Planar Electrode Emitter," Anal. Chem., 74:5047-5056, 2002.

Whitt et al., "Capillary electrophoresis to Mass Spectrometry Interface Using a Porous Junction," Anal. Chem., 75(9):2188-2191, 2003.

Xu et al., "A microfabricated dialysis device for sample cleanup in electrospray ionization mass spectrometry," Anal. Chem., 70(17):3553-3556, 1998.

Supplementary European Search Report dated Nov. 11, 2010 from corresponding EP Application No. 07837354.5 (6 pages).

U.S. Appl. No. 13/070,010, filed Mar. 23, 2011, Whitehouse et al.

SAMPLE COMPONENT TRAPPING, RELEASE, AND SEPARATION WITH MEMBRANE ASSEMBLIES INTERFACED TO ELECTROSPRAY MASS SPECTROMETRY

RELATED PATENTS AND PATENT APPLICATIONS

This application is a continuation of U.S. application Ser. No. 11/895,494, filed Aug. 24, 2007, now U.S. Pat. No. 7,872,225, which claims priority to U.S. Provisional Patent Application Ser. No. 60/840,095, filed on Aug. 25, 2006. U.S. Pat. No. 7,872,225 is also a continuation-in-part of U.S. patent application Ser. No. 11/803,984, filed on May 15, 2007, now U.S. Pat. No. 7,619,216, which is a continuation of U.S. patent application Ser. No. 11/132,953, filed on May 19, 2005, now U.S. Pat. No. 7,232,992. The contents of both U.S. Provisional Patent Application Ser. No. 60/840,095 and U.S. patent application Ser. No. 11/803,984 are incorporated herein by reference. U.S. Pat. No. 4,542,293 is also incorporated herein by reference.

FIELD OF INVENTION

This invention relates to the field of separation of sample components using electric fields and ion currents in solution with remote cation and/or anion species generation in solution flows off-line with non Mass Spectrometer detectors or integrated on-line with Electrospray Ionization or other Atmospheric Pressure Ion Source interfaced to a Mass Spectrometer.

BACKGROUND

The invention includes apparatus and methods that enables or enhances capture, release and/or separation of analyte compounds in a sample solution using electric fields and ion current flow through the sample solution channel with cation and/or anion exchange through semipermeable membranes with multiple second solution flow paths. Cations or anions generated or present in the sample solution or in one or more second solution flow paths are transferred through ion selective semipermeable membranes into or out of the sample solution flow channel to effect trapping, electrocapture, binding, displacement, release and/or isoelectric focusing of sample components in the sample solution. The invention comprises a stand alone separation method and apparatus using non mass spectrometer detectors or may be connected to or integrated with an Electrospray Ionization or other Atmospheric Pressure ion source interfaced to a Mass Spectrometer analyzer. The invention apparatus and methods may be scaled to accommodate higher or lower sample solution liquid flow rates.

The invention may be configured in a high pressure liquid chromatography (HPLC) apparatus and methods with packed columns or can be applied to methods and apparatus employing low pressure packed or open tubular column sample separation techniques. The invention comprises one or more semipermeable membrane assemblies positioned along a sample solution flow channel with membrane assemblies separating a sample bearing first solution from one or more second solution flows. Each second solution flow can have a different composition and each second solution composition can change over time using solution composition gradients or step functions. Packed or open channels, where sample component separation occurs, may be configured in a membrane assembly, between membrane assemblies or positioned upstream or downstream of membrane assemblies. Ions generated in the second solution flow paths are transferred through the semipermeable membrane into the sample solution flow driven by the applied electric field. Conversely, ions in the sample solution can be transferred into a second solution through the semipermeable membranes. Ions can be selectively added to or removed from the sample solution flow path at one or more membrane sections positioned along the sample solution flow path. The ion current passing through the semipermeable membrane into the sample solution is subsequently driven along the length of the sample solution channel by a voltage gradient maintained along a portion of the sample solution flow channel length. Individually controlled voltages are applied to electrodes in contact with each second solution flow. Multiple semipermeable membrane sections positioned along the sample solution flow path allow the application of different electric fields and ion currents at different locations in the sample solution flow path. Ions entering the sample solution through one membrane can be remove through an adjacent membrane along the sample solution flow path forming local trapping, capture, release or separation regions.

Configuring one or more semipermeable membrane sections with Electrospray ionization allows independent control and optimization of the capture, trapping, release and/or separation of sample species and Electrospray ionization. Membrane materials and second solution compositions may also be configured to allow selected neutral species to traverse a membrane from a second solution into the sample solution or conversely from the sample solution into a second solution. The transfer of neutral species through a semipermeable membrane is driven or controlled by controlling the relative concentration of the neutral species of interest across each membrane. The added ion or ion and neutral species selectively introduced into or removed from the sample bearing first solution changes the solution pH and/or solution chemistry causing or enhancing binding or release of sample components and effecting separation, cleanup or reactions of analyte species. These processes can also be used to simultaneously optimize or enhance the performance if an Atmospheric Pressure Ion (API Source) such as Electrospray.

Separations of mixtures of analyte components in a solution is widely practiced using packed Liquid Chromatography (LC) separations, open tube Capillary Electrophoresis (CE) and more recently open tube Electrocapture (EC). Liquid Chromatography separation is effected by binding or partial binding of an analyte to a solid phase or material packed within the chromatography column as a liquid or mobile phase flow passes through the column. The liquid flow through the column can be run isocratically, having constant composition, or with changing composition, usually in the form of a gradient or a series of steps. When running isocratic liquid chromatography, analytes are separated in the flowing solution by size differences or differences in partial binding energy with the surface chemistry or phase of material packed within the liquid chromatography column volume. Analyte species that exhibit stronger binding to the column phase will elute from the column at a later time then those analytes with weaker binding energy. Analyte components eluting from a chromatography column are separated both spatially in the solution flow and temporally. When gradient liquid chromatography separations are conducted, the chemistry of the solution passing through the column is varied in a controlled manner to release analyte bound to the column phase material at specific times. Analytes with different binding energies and/or different solution chemistry release conditions will be separated in solution flowing through the liquid chromatography column. Separation of analytes in solution occur due to the partitioning of attractive and release forces on a given analyte species based on the differential interactions between the stationary and mobile phases in a liquid chromatography column. Attractive and release forces are manipulated by changing solution polarity, pH and ionic or buffer species concentration. Analytes are separated in open tube Capillary Electrophoresis and Electrocapture by a balance of electric fields, ion mobility and in the case of Electrocapture, convective solution flow.

The most commonly used types of high pressure liquid chromatography include Reverse Phase (RP), Normal Phase (NP), Ion Exchange (IE) and Size Exclusion (SE) separations. None of these separation techniques are practiced with an ion current passing through the LC column. Capillary Electrophoresis (CE) employs an electric field maintained in the sample solution along an open CE column length to effect separation of analyte species through differential electroosmotic migration of analyte species through a solution with electroosmotic flow (EOF) along the CE column length. Variations in Capillary Electrophoresis have been developed, such as Capillary Electrochromatography (CEC), that combine use electroosmotic separation of CE with the partitioning separation of LC due to differential interactions between two phases. Typically in CE and CEC the sample solution composition remains constant throughout a separation run. Semipermeable membranes have been configured by Severs J. C., and Smith R. D., Anal. Chem. 1997, 69, 2154-2158, at the exit end of CE columns to complete the electrical circuit in a CE-Electrospray Mass Spectrometer interface. Capillary electrophoresis separation of analyte species was used in this apparatus and method. No liquid chromatography separation was described using this interface and no ion species passing through the membrane flowed through the CE column to enhance or cause species separation in solution.

Electrocapture of sample components in solution has been employed to capture sample components in an open column liquid flow stream with subsequent release of components. Electrocapture or analyte species in an open liquid flow column or channel allows preconcentration of samples prior to separation with CE, sample preparation such as desalting, reaction with reagent species and effecting separation of components in the solution flow as described by Juan Astorga-Wells et. al., U.S. Pat. No. US 2005/0284762 A1, Sag-Ryoul Park and Herold Swerdlow, Anal. Chem. 2003, 75, 4467-4474 and Juan Astorga-Wells, Hans Jornaval, and Tomas Bergman, Anal. Chem. 75, 5213-5219. Electrocapture of species is effected using a balance of electric fields, ion mobility and hydrodynamic flow along a liquid flow channel length. Semipermeable membranes separating the sample solution flow from anode and cathode electrodes immersed in reservoirs containing static conductive solutions with no flow have been configured in Electrocapture devices as described in the above references. As described by the authors, sample components in solution have been captured with hydrodynamic forces balanced against an electric field along the sample flow path or on a semipermeable membrane. Release of components can be realized by changing the voltage between the anode and cathode, changing the sample solution flow rate and/or changing the sample solution composition. The Electrocapture devices have no second solution flow to replenish charge in the anode and cathode reservoirs. When the sample flow is stopped, the current in the sample flow channel stops due to charge depletion. In the present invention, second solution flow supplies charged species to the sample solution flow path through the semipermeable membranes and replenishes the charge during operation. The present invention requires no electrolytes added to the sample solution and the electrical current maintained along the sample solution flow path can be changed by modifying the second solution composition with no need to change relative electrode voltage or no requirement to change the composition of the sample solution flow to effect capture and/or release of analyte components in the sample flow.

The use of semipermeable membranes to exchange unwanted ion species in an eluant flow eluting from a liquid chromatography column with a desired ion species has been described previously in EPA Publication Numbers 32,770, 69,285 and 75,371, 69,285 and 180,321 with publication dates Jul. 29, 1981, Jan. 12, 1983, Mar. 30, 1983 and May 7, 1986 respectively. This technique generically described as ion suppression is widely practiced in ion exchange chromatography (IEC) to reduce the conductivity of eluant exiting an IEC column prior to passing through a conductivity detector. Separation is often achieved in IEC by displacing analyte bound to the column stationary phase by charge with a displacing anion or cation added to eluant flow. The anion or cation species, typically added as a net neutral salt, hydroxide or acid compound to the eluant flow passing through an IEC column, can be removed after the IEC column exit by charged species exchange through flat or cylindrical semipermeable membranes as described in the above EPA publications. The selective reduction of solution conductivity without the reduction of analyte species in IEC eluant flow improves the conductivity detection limits of analytes separated while passing through an IEC column. Dual membrane devices are configured wherein the eluant flow exiting the IEC column is in contact with two semipermeable membranes which separate the eluant liquid from two second solutions flowing on the opposite side of both membranes. A voltage is applied between electrodes in contact with both second solution flows driving charged species of one polarity from one second solution flow into the eluant flow while simultaneously driving a charged species in the eluant flow through the second membrane into the second eluant flow. This effectively exchanges charged species in a net neutral eluant flow between the IEC column exit and a conductivity detector. Multiple layer membrane assemblies have been configured to provide exchange or suppression of charged species in eluant flow exiting an IEC column while regenerating the second solution neutral salt, acid or base composition used to exchange ion species.

Similar semipermeable membrane devices have been configured to provide selected cation or anion species with counter ions in aqueous eluant flow as described in U.S. Pat. No. 5,045,204. Two or more membrane assemblies have been configured in contact with the eluant exiting from an IEC column providing the dual function of exchanging ion species to reduce conductivity while simultaneously adding the removed ion species combined with a counter ion to an aqueous solution. The aqueous solution with the neutral salt, acid or base species is used as the eluant flow entering the IEC column as described in U.S. Pat. No. 5,045,204. The exchange of ion species, as described, occurs in an ion exchange resin bed configured downstream of the IEC column exit and after the region of chromatography separation in an ion chromatography system. No ion current passes through the separation or LC column or separation media. In the apparatus and methods described, a net electrically neutral fluid flow passes through the IEC column and no ion current passes through the IEC column. Gradients of ion species with counter ions can be generated post column in the IEC eluant flow exiting the IEC column by increasing the ion current passing through the semipermeable membranes. This is effected by changing second solution composition or the electrical potential applied between electrodes in contact with the second solutions.

The present invention provides the addition and/or removal of charged species through one or more semipermeable membranes to an eluant flow through a liquid chromatography column, an Ion Exchange column, a CE column and/or an Electrocapture flow channel. The invention provides direct ion current through an LC or IEC column or through an unpacked channel. No counter ion is added to the eluant flow and the addition of charged species to the eluant flow through the semipermeable membranes matches the electrical current passing through the LC or IEC column or open sample solution channel length. Charged species added from one second solution into the sample solution eluant flow through a first semipermeable membrane can be removed by passing equal ion current from the sample solution through a second semipermeable membrane into a different second solution flow positioned at the opposite end of the LC, IEC column or open channel. The semipermeable membrane materials and second solution compositions can be selected to introduce charged species and/or organic modifiers into the eluant flow from one or more second solution flows to effect or improve ion exchange, reverse phase chromatographic, CEC or Electrocapture separation of analyte species in solution.

In different embodiments of the invention one or more membrane assemblies are configured with an Electrospray (ES) ion source or other API source interfaced to a mass spectrometer (MS). Such embodiments of the invention can be configured wherein sample separation can be performed integrated with the Electrospray process or the sample separation process can be conducted and optimized independent from Electrospray Mass Spectrometer (ES/MS) processes. Embodiments of the invention provide an efficient and precise means of adding charged species to an eluant flow to effect or enhance chromatographic or Electrocapture separation while simultaneously optimizing Electrospray ionization source mass spectrometer performance. Configuring an Electrospray ion source with a semipermeable membrane assembly whereby Electrospray current is generated in a second solution flow and transferred through the semipermeable membrane is described in U.S. Pending patent application Ser. No. 11/132,953 included herein by reference.

SUMMARY OF THE INVENTION

The present invention enables the controlled addition and removal of ion or neutral species into eluant flow without counter ions or the exchange of ions of like charge in liquid chromatography, IEC or Electrocapture packed or open solution channel analyte species separations. Ion or neutral species are transferred through one or more semipermeable membranes between a sample solution and one or more second solution flows to effect sample component capture, release and separation in the sample solution flow path while enabling optimization of Electrospray ionization and mass spectrometer performance. The invention can be configured with electrical current passing through the sample solution flow channel packed with separation media or configured as open flow channel. Cation or Anion species pass through the packed LC column or open sample solution flow path as electrical current in direct proportion to the electrical current passing through the semipermeable membranes positioned upstream and downstream in the sample solution flowpath. For a given sample solution composition, the ion current and ion species passing through the packed or open sample solution flow channel can be controlled by adjusting the voltage applied to electrodes in the second solution flowpaths of membrane assemblies and/or changing the composition of the second solutions through gradients or step functions. The total Electrospray current can be controlled independent of the direction or magnitude of the upstream ion current passing along the sample solution flow path. Single or multiple semipermeable membrane assemblies can be configured with one or more sections of packed and/or open sections of sample solution flow path and with one or more detectors including ultraviolet light absorption, conductivity, condensation nuclei and mass spectrometer detectors. The invention can be configured with or integrated into an Electrospray ion source or other API source interfaced to a mass spectrometer. The independent control of ion current, cation or anion species and sample solution composition in the sample solution flow channel and into specific LC, IEC, CE or CEC column and detector types allows independent optimization of sample component separation and detector performance.

The invention provides independent adjustment of the following variables to optimize sample component trapping, release and/or separation in solution while independently optimizing Electrospray or other API source and Mass Spectrometer or other detector performance;

1. Second solution composition can be changed independently using gradients and/or step functions in each membrane assembly during a run.
2. Relative voltage amplitude and polarity applied to electrodes in second solution flow paths of adjacent membrane assemblies can be independently adjusted during a run.
3. Semipermeable membrane materials can be configured to pass selected ion and/or neutral species.
4. The sample solution composition can be changed using a gradient or a step function during a run.
5. The relative voltages applied to Electrospray ion source or other API source electrodes can be changed independently of upstream second solution electrode voltages.

Each voltage, and solution composition variable can be independently controlled in a synchronized manner through manual or programmed software control.

The invention comprises different combinations and configurations of membrane assemblies, packed sections and open sections of the sample solution flow path, Electrospray probe assemblies configured with and without pneumatic nebulization assist and different detector types including but not limited to mass spectrometry, UV absorption, conductivity and particle counting. Embodiments of the invention can include but are not limited to the following component combinations:

1. A single semipermeable Membrane assembly positioned upstream of an Electrospray inlet probe with the Electrospray spray sample solution flow tube comprising a packed LC column.
2. Two semipermeable Membrane assemblies configured at the entrance and exit end of a packed LC column with an Electrospray inlet probe positioned downstream of the exit end Membrane assembly.
3. Three semipermeable Membrane assemblies with downstream Membrane assembly one providing Electrospray ion current and a packed LC column configured between the upstream Membrane assemblies two and three configured in series along the sample solution flow path.
4. Three semipermeable Membrane assemblies with the first downstream Membrane assembly providing Electrospray ion current and an open sample solution flow channel configured between upstream Membrane assemblies two and three configured in series along the sample solution flow path.
5. Three semipermeable Membrane assemblies with the first downstream Membrane assembly providing Electrospray ion current, a packed or open sample solution flow channel configured between the second and third upstream Membrane assemblies and an Ultraviolet light absorption detector cell positioned between the first and second Membrane assembly in the sample solution flow path.
6. Four semipermeable Membrane assemblies configured in the sample solution flow path with the first down stream Membrane assembly providing Electrospray ion current and with open channel sections of the sample solution flow path configured between upstream Membrane assemblies 2 and 3 and 3 and 4 respectively.
7. Four semipermeable Membrane assemblies configured in the sample solution flow path with the first down stream Membrane assembly providing Electrospray ion current and a packed LC column configured between upstream Membrane assemblies three and four and an open sample solution channel section configured between upstream Membrane assemblies two and three.

The configuration and operation of each embodiment of the invention listed above may be varied. The Electrospray (ES) ion source interfaced to a mass spectrometer may be replaced with alternative Atmospheric Pressure Ion Sources, Including but not limited to Atmospheric Pressure Chemical Ionization (APCI), Photoionization (PI), combination ES and APCI, Desorption Electrospray Ionization (DESI) or Direct Analysis in Real Time (DART). The Electrospray ion or API source interfaced to Mass Spectrometer may be replaced with alternative detectors including but not limited to conductivity, light adsorbing and condensation nuclei particle counting detectors. The Electrospray probe may be operated at close to ground potential or at higher voltage. The LC or IC column packing material may comprise reverse phase, normal phase, ion exchange media or affinity chemistries. The semipermeable membranes may be configured with the same or different materials in the same apparatus. The second solution composition flowing through each Membrane assembly in the same apparatus may be comprised of different compositions with each second solution composition changing independently during a run. In all embodiments of the invention, the sample solution flow composition can be changed using gradients or step functions independent of but synchronized with other variable value changes in the same apparatus.

Embodiments of the invention can be configured to provide different means of selectively capturing, releasing and/or separating sample component species in the sample solution flow path. Selectively capturing sample components in traditional LC, IEC and Electrocapture techniques provides a means for desalting, preconcentrating or reacting sample components prior to separation or fraction collection. For example, reactions with trapped or captured analyte components can be conducted by adding reagent species to effect deuterium exchange or a tryptic digest of a protein. Using the invention, sample components in solution can be captured, released and/or separated and analyzed and detected using multiple function apparatus which provides additional control of processes and new analytical methods compared to traditional LC, IEC, CE or Electrocapture techniques. Sample components separated using the invention may be detected and analyzed on-line and/or fraction collected for off-line analysis. The invention allows capture or adsorption of sample components in the solution flow using one or more of the following methods:
1. Binding through ion-ion interaction between a solid packing phase and the sample components in solution when using an IEC packing media.
2. Adsorption between a solid packing phase and the sample components in solution similar when using reverse phase and normal phase chromatography packing media.
3. Electrocapture in open flow channels between membrane assemblies and
4. Adsorption on membrane surfaces due to electrostatic forces and/or membrane surface coatings.

The invention allows the release of adsorbed or electrocaptured sample components in the sample solution flow channel using one or more of the following methods:
1. Displacement of ion-ion interaction sample components by a displacing anion or cation passing through the IEC packed column as ion current in the sample solution flow path. The ion current intensity, direction and composition can be changed by changing adjacent second solution composition or relative voltages applied to electrodes and/or by changing the sample solution composition.
2. Changing pH in a packed IEC, RP or NP column by increasing or decreasing the proton ion current ($H^+$) passing through the column in the sample solution flow path. Ion current is increased or decreased by changing second solution compositions, relative voltages and/or sample solution composition.
3. Changing organic solvent concentration in the packed or open columns configured in the sample solution flow path by changing the second solution solvent composition and/or the sample solution composition.
4. Changing the ion current polarity and/or intensity passing through an open channel section between membrane assemblies by changing second solution compositions, relative voltages and/or sample solution composition or flow rate.
5. Changing the ion current direction, intensity or composition passing through a membrane by changing the membrane assembly second solution composition or relative electrode voltages between adjacent membrane probe assemblies.

The invention allows the separation of sample components in the sample solution channel by:
1. Selectively adsorbing and releasing sample components in pack columns using one or more methods listed above. Changing ion current or ion composition through the packed columns by ramping or stepping adjacent second solution compositions and/or relative voltages.
2. Selectively Electrocapturing and releasing sample components in open sample solution flow paths using one or more methods listed above.
3. Running capillary electrophoresis in the sample solution flow path by applying the appropriate voltages to one or more semipermembrane assembly second solution electrodes in the sample solution flow path or by ramping or stepping changing second solution composition.
4. Running Capillary Electrochromatography in open or packed channel sections between one or more membrane probe assemblies.

Electrospray or API source operation can be effectively decoupled from the upstream sample component, capture, release and separation functions and local section ion currents by configuring the ES inlet probe with a separate semipermeable Membrane assembly. The separate ES Membrane assembly second solution composition and second solution electrode potential can be set to effectively isolate the ES operation from upstream Membrane assembly generated ion currents in the sample solution flow path. Positive or negative ion polarity can be Electrosprayed with this invention without modifying upstream capture, release or separation conditions. This is achieved by switching the Electrospray ion source counter electrode voltage polarity while applying a voltage near ground potential to the Electrospray membrane probe assembly second solution electrode.

Embodiments of the invention comprising one or more membrane assembly sections, packed LC columns and/or open channel sections of the sample solution flow path may be configured in a single integrated assembly including an Electrospray inlet probe or alternatively may be configured as discrete subassemblies. Integrated and discrete assemblies can be scaled up or down in size and sample solution flow rates to accommodate specific analytical applications. Membrane assemblies may comprise tube shaped or flat semipermeable membrane geometries. In alternative embodiments of the invention, packed LC columns may be integrated into the membrane assemblies to reduce dead volume and improve separation efficiency. In such integrated membrane and LC column embodiments, fast ion current gradients are possible with the LC packing material in direct contact with semipermeable membrane. Second solution flow may be operated in higher pressures in one or more Membrane assembly using the sample solution pressure to reference the second solution downstream pressure. This configuration minimizes or eliminates any pressure gradient from forming across a semipermeable membrane at the entrance end of packed LC or IEC column. Minimizing or eliminating the pressure gradient across a semipermeable membrane reduces the risk of membrane failure and optimizes the effectiveness of the membrane selectivity. In embodiments of the invention, the input sample solution flow composition may be run isocratic or as a gradient during an LC, IEC, CE CEC or Electrocapture separation. Ion current gradients run through semipermeable membranes can be synchronized with a sample solution composition gradient to improve LC separation efficiency.

DETAILED DESCRIPTION OF THE INVENTION

The present invention comprises one or more semipermeable Membrane assemblies configured along a sample solution flow path that includes packed or open channel sections. Embodiments of the invention comprise interfacing with Electrospray inlet probes or other API source types interfaced to mass spectrometers. Selected ion species pass through one or more semipermeable membranes into or from one or more second solution flow channels and into or from a sample solution flow. Such ion species form an ion current along the sample solution flow path that may include a packed or open channel section or an Electrospray probe or an inlet probe to an alternative API source type. Some embodiments of the invention comprise at least one set of adjacent semipermeable Membrane assemblies connected by a packed or opened channel sample solution flow path. During operation, a voltage difference is maintained between the electrodes positioned in the second solution flow channels of each adjacent Membrane assembly. The voltage differential between Membrane assemblies drives the generation of cations or anions ions at the second solution electrode in the first Membrane assembly and the passing of such ions through the first semipermeable membrane into the sample solution flow path. The electric field continues to drive the cations or anions along the sample solution flow path through a packed or open channel section. The same electric field then directs the cation or anion current from the sample solution flow path through the second Membrane assembly semipermeable membrane to the second solution electrode. The cation or anion composition and current passing through the sample solution packed or open channel can be controlled to effect selective sample or analyte species capture, release and/or separation on line with Electrospray ionization and Mass Spectrometric analysis. Alternatively other detectors and/or fraction collectors including, but not limited to, conductivity or light absorption detectors may be interfaced to the semipermeable Membrane assembly apparatus to detect or collect eluting sample species. Different embodiments of multiple solution flow channel semipermeable Membrane apparatus and operating methods are described in U.S. patent application Ser. No. 11/132,953 incorporated herein by reference. Although specific configurations of semipermeable Membrane assemblies are described in embodiments of the present invention, alternative semipermeable Membrane assemblies described in U.S. patent application Ser. No. 11/132,953 may be configured as alternative embodiments of the invention.

Figure 1:
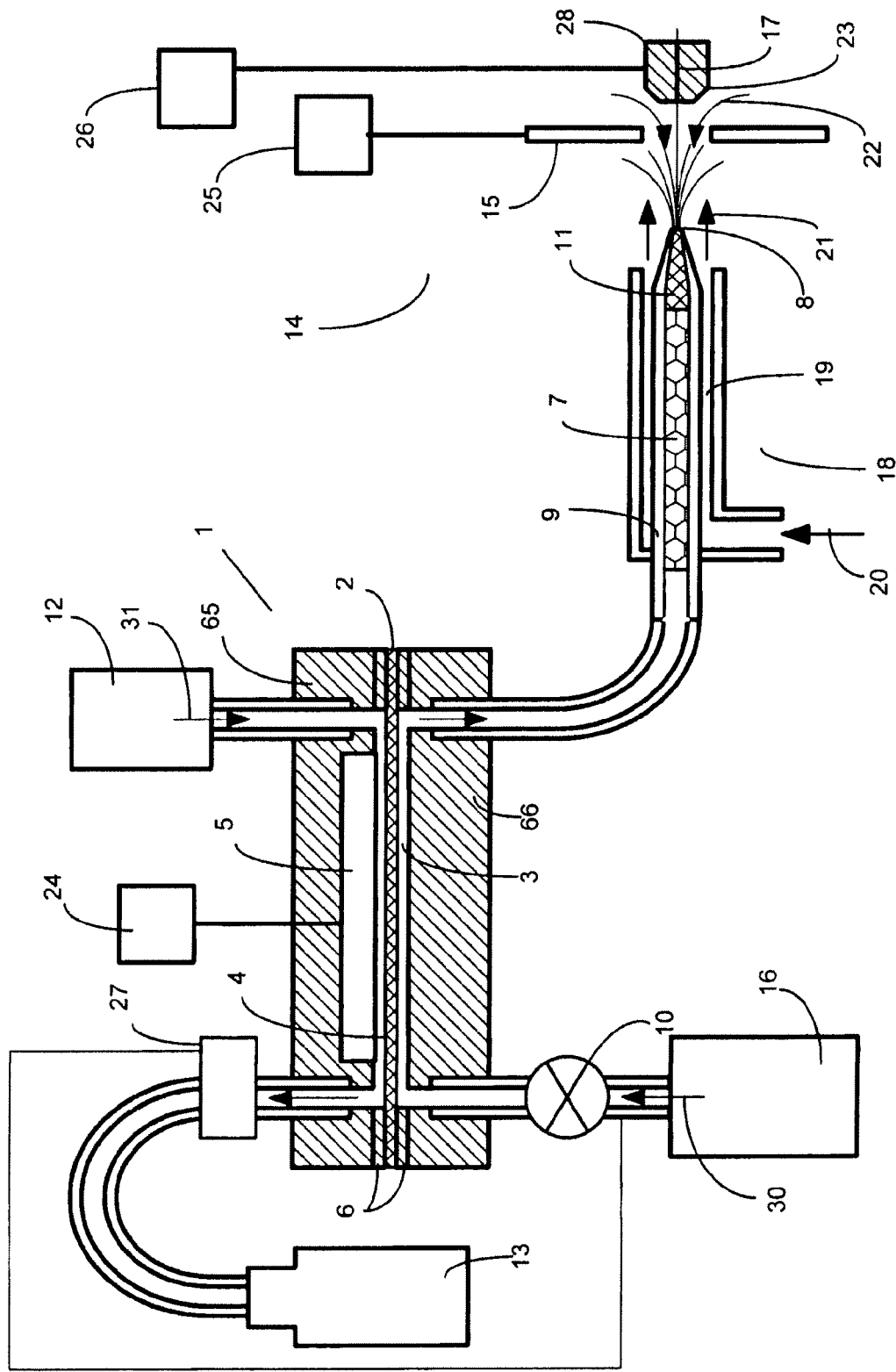
FIG. 1 is a diagram of a packed LC column integrated into an Electrospray inlet probe positioned downstream of a single semipermeable Membrane assembly.

One embodiment of the invention comprising a single Membrane assembly and a packed separation column interfaced to an Electrospray ionization source is diagrammed in FIG. 1. Referring to FIG. 1, in Membrane assembly 1, sample solution flow channel 3 and second solution flow channel 4 are separated by semipermeable membrane 2. In the embodiment shown, no electrically connected conductive surfaces are configured in the sample solution flow path. This prevents reduction and oxidation (redox) reactions from occurring in the sample solution flow path 3 during Electrospray ionization operation. Isocratic or gradient sample solution flow is delivered by fluid delivery system or pump 16 into sample solution flow channel 3 through sample injector valve 10. Sample solution 30 passes through flow channel 3 in contact with semipermeable membrane 2 and flows through packed or monolithic column 9 comprising RP, NP or IEC packing material 7, frit 11 and Electrospray tip 8. A second solution flow 31 is delivered from gradient fluid delivery system 12, passes through second solution flow channel 4 in contact with semipermeable membrane 2 and electrode 5 and flows into waste bottle 13. Packed separation column 9 integrated with Electrospray tip 8 is configured in Electrospray inlet probe 18 comprising pneumatic nebulization annulus 19 with nebulization gas inlet 20 and exit 21. Sample solution flow passing through packed or monolithic column 9 may produce back pressure in sample solution flow path 3. Back pressure regulator 27 references the pressure at the exit of flow channel 3 and regulates the pressure in second solution flow channel 4 to minimize or eliminate any pressure gradient across semipermeable membrane 2 during operation. Minimizing or eliminating any pressure gradient across semipermeable membrane 2 avoids rupture of the membrane and/or reduction of its selectivity function.

Electrospray inlet probe 18 is configured in Electrospray ion source 14 with endplate electrode 15, capillary orifice 17 into vacuum, capillary entrance electrode 23 and heated counter current drying gas 22. Electrodes 5, 15, and 23 are connected to dual polarity voltage supplies 24, 25, and 26 respectively. A portion of the ions generated in Electrospray source 14 are transferred into vacuum through capillary orifice 17 where they are mass to charge analyzed.

As described in U.S. patent application Ser. No. 11/132, 953, a voltage is applied between Membrane assembly electrode 5 and counter electrodes 15 and 23 to form an electric field at Electrospray tip 8. For positive ion polarity Electrospray ionization, Membrane assembly electrode 5 can be operated at or near ground potential with the endplate electrode 15 and capillary entrance electrode 23 operated a negative kilovolt potentials. Positive polarity ions entering dielectric capillary 28 orifice 17 at negative kilovolt potentials can be transferred into vacuum and exit at ground or hundreds of volts above ground. Negative polarity ions can be generated in ES ion source 14 by reversing the polarity of each electrode. The method of changing ion potential energy in dielectric capillaries allowing Electrospray probes to be run at or near ground potential in either ion polarity is described in U.S. Pat. No. 4,542,293 incorporated herein by reference. Alternatively, Membrane assembly electrode 5 can be operated at kilovolt potentials and capillary entrance electrode 23 at or near ground potential provided second solution fluid delivery system 12 and reservoir 13 are electrically isolated. Nozzle orifices and heated metal capillary orifices into vacuum configured in Electrospray or other types of API sources are typically operated at or near ground potential. The invention can be configured with grounded orifice into vacuum or dielectric capillary 28 whose entrance electrode 23 can be operated at a voltage range from ground to +/− kilovolt potentials. The dielectric capillary offers performance advantages when configured with the invention as the relative voltages between electrodes 5, 15 and 23 can remain constant or independently optimized even when stepping or scanning the voltage applied to Membrane assembly electrode 5. Consequently, the Electrospray ion source performance remains optimized during upstream sample species trapping, release and separations operation using the invention described herein.

Figure 2:
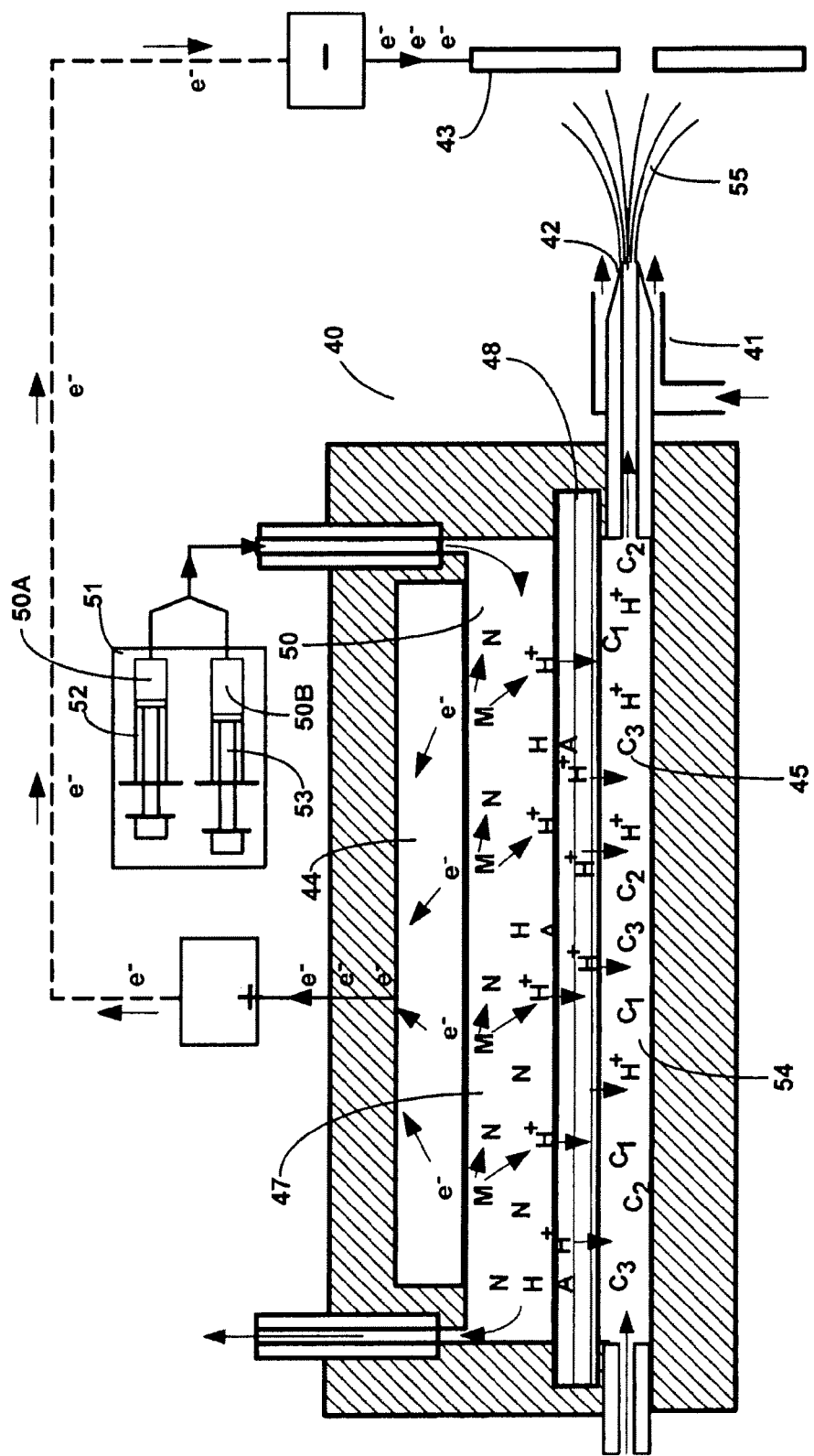
FIG. 2 is a diagram of one example of ion and electrical current through a semipermeable Membrane assembly interfaced to an Electrospray inlet probe.

Trapping, release and separation of sample species using the embodiment of the invention shown in FIG. 1 is achieved by ramping or stepping the Electrospray ion current, by modifying the sample solution chemistry or a combination of both. FIG. 2 is a diagram of the basic operation of the Membrane assembly 40 interfaced to Electrospray probe with pneumatic nebulization assist 41 during positive ion polarity Electrospray. No electrically connected conductive surfaces are configured in sample solution flow path or Electrospray inlet probe 41. This prevents redox reactions from occurring on conductive surfaces along the sample solution flow path during Electrospray operation. A negative voltage is applied to endplate or counter electrode 43 and ground or a positive voltage is applied to Membrane assembly electrode 44 during Electrospray operation. The voltage difference applied between electrodes 43 and 44 will range from kilovolt potentials to hundreds of volts depending on the distance between Electrospray inlet probe tip 42 and endplate electrode 43. The voltage difference between electrodes 44 and 43 forms an electric field at Electrospray probe tip 42 that is maintained below the onset of corona discharge or gas phase breakdown. The onset of corona discharge sets an upper bound for the relative ES voltages applied and constrains the ability to change total Electrospray current by adjusting Electrospray electrode voltages. The electric field maintained at Electrospray probe tip 42 is conducted through sample solution flow channel 45, semipermeable membrane 48 and second solution flow channel 47 to electrode 44. The total Electrospray current is a function of the electric field at ES probe tip 42 and the total resistance, or inversely conductivity, through the path from ES probe tip 42 to Membrane assembly electrode 44. The conductivity of the liquid conductance path is changed by modifying the composition of second solution 50 flowing through second solution flow channel 47 and/or the composition of sample solution 54 flowing through channel 45. The composition of second solution 50 can be changed using gradients or step functions delivered from fluid delivery system or dual syringe pump 51. Syringe 52 delivers second solution 50A and Syringe 53 delivers second solution 50B. Each syringe delivery rate can be set or ramped independently with manual or software control to generate any ratio of solutions 50A and B while retaining a constant total second solution flow through second solution flow channel 47. In the example shown in FIG. 2, second solution 50A comprises 100% water and solution 50B comprises water with 10% acetic acid. As second solution 50 composition is ramped from 100% water (only second solution 50A is delivered) to increasing concentrations of acetic acid in water (mixture of second solutions 50A and B), the total Electrospray current can be scanned from approximately 15 nanoamps to over one microamp.

Due to the applied electric field, protons are formed through electrolytic processes occurring at the surface of Membrane assembly electrode 44. The protons formed pass through membrane 48, driven by the applied electric field into sample solution flow channel 45. The surface of Membrane assembly electrode 44 may comprise, platinum, gold, carbon, stainless steel or other conductive material. Materials such as platinum or carbon are preferred to avoid electrolytic erosion of the electrode surface during operation and to avoid generating undesired cations or anions from the electrode material that may migrate through semipermeable membrane 48. For the positive ion polarity example diagrammed in FIG. 2, the total Electrospray current essentially equals the total proton ion current passing through cation exchange membrane 48. Cation exchange membranes do not entirely block the transfer of some anions moving from sample solution 54 into second solution 47, driven by the electric field, but the contribution to the total current passing through electrode 44 is quite small. In the example shown, cation exchange membrane 48 comprises sulfonated fluoroethylene material (perfluorosulfonic acid polytetrafluoroethylene (PTFE) copolymer) one formulation of which is Nafion® (® Dupont). Other membrane materials can be configured in Membrane assemblies including but not limited to cellulose esters, polysulfone dialysis tubing with different molecular weight cutoffs, cation or anion exchange semipermeable membranes available from Dionex Corporation and cation exchange membranes from RAI Research Corporation (Raipore R4010 and R1010). As diagrammed in FIG. 2, electrolysis occurring at the surface of Membrane assembly electrode 44 produces protons that are transferred through cation exchange membrane 48 driven by the electric field into sample solution flow channel 45. The protons move with sample solution flow channel 45, driven by the flow of sample solution 54 and the Electrospray electric field, and exit through Electrospray probe tip 42. The protons formed at Membrane assembly electrode 44 provide essentially the total Electrospray charged droplet current formed in Electrospray 55. Consequently, as the total Electrospray current increases, the pH of sample solution 54 decreases in sample solution flow channel 45 between semipermeable membrane 48 and Electrospray probe tip 42.

PH scans in sample solution 54 can be conducted from lower to higher pH or higher to lower pH by running a gradient or step function of acid concentration in second solution 50. PH is defined as the log of proton or H+ concentration or molarity in solution, so a ten times increase in Electrospray total ion current corresponds to a one unit drop on the pH scale. Running Electrospray with pneumatic nebulization assist, a range of total Electrospray current covering over three orders of magnitude can be achieved using the embodiment of the invention as shown in FIG. 2. Sufficient membrane area in contact with sample solution 54 and second solution 50 is needed to support higher current operation. Scanning Electrospray total ion current over three orders of magnitude, the pH in the sample solution is scanned over a 3 pH units range. For example, if sample solution 54 is 100% aqueous, a pH scan in the sample solution can range from just below pH 7 to pH 4. When negative ion polarity Electrospray is run using a cation exchange membrane 48, protons are removed from sample solution 54 as it flows through sample solution flow channel 45. As the negative ion polarity total Electrospray current is increased, the pH in sample solution 54 increases. In the case of a 100% aqueous sample solution 54 a pH scan ranging from approximately 7 to above 9 could be conducted by increasing the acid concentration or conductivity of second solution 50. If it is desirable to scan through a different region of the pH scale, the sample solution can be buffered to a desired pH with an appropriate buffer concentration added to sample solution 54. Increasing the Electrospray current while running the buffered sample solution, by increasing acid concentration in second solution 50, changes the pH from the initial buffered pH value.

Alternately, concentrations of bases or salts added instead of acids to second solution 50 can be changed by running concentration gradients flowing through second solution flow channel 45. By selecting the appropriate cation or anion exchange membrane and appropriate solvents, specific cations such as sodium or potassium can be transferred through semipermeable membrane 48 instead of protons. For many Electrospray applications, sodium or potassium may not be the preferred charge carrier species but, as will be described for different embodiments of the invention, such cations may be a preferred species to displace bound sample components when IEC packing materials are used. Controlling sample solution pH can also be used in certain applications to initially promote capture or binding of sample species on an RP or IEC packing material and subsequently releasing the bound sample species by changing the solution pH. Using the embodiment shown in FIG. 1, packing material 7 can be selected to binding sample species at an initial pH established by the Electrospray current and release the bound sample species at a different pH established using a different Electrospray current. This method can be used for cleanup, desalting or separation of sample components. Bound sample can also be subjected to reactions by changing the sample solution composition and maintaining constant total Electrospray current. Alternatively, the conductivity and organic solvent concentration can be stepped or ramped in second solution 50. With the selection of the appropriate semipermeable membrane, organic solvent will pass through the membrane driven by concentration gradients across the membrane to improve the efficiency or release of sample species bound to packing material 7, complimenting or enhancing a pH gradient. The composition of sample solution 54 and second solution 50 can be changed independently to most efficiently accommodate online sample cleanup and/or separation of sample species in the embodiment of the invention shown in FIG. 1.

Figure 3:
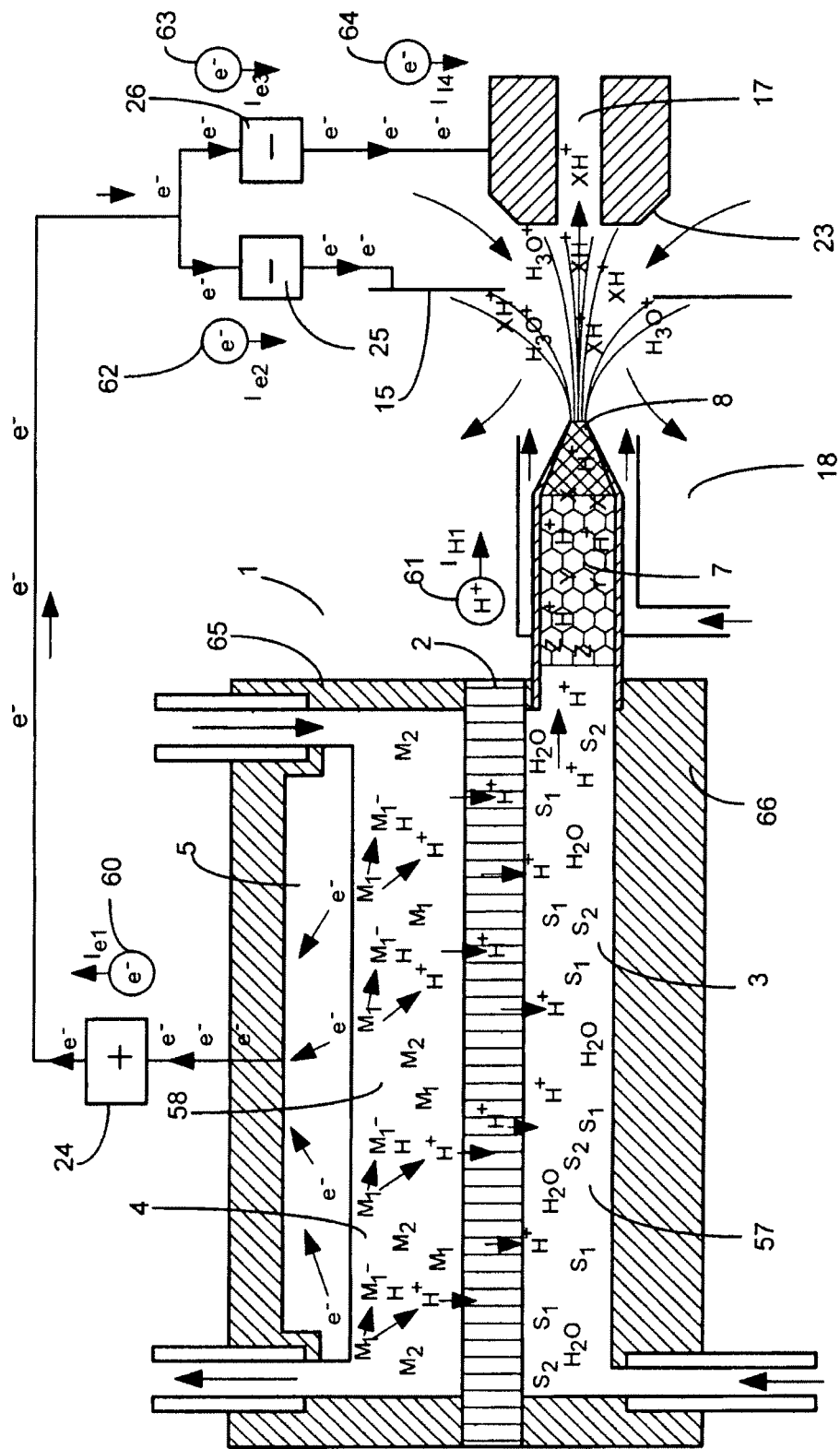
FIG. 3 is a diagram of the ion and electrical flow through a semipermeable Membrane Electrospray probe configured with the embodiment shown in FIG. 1.

The ion and electrical current pathways occurring in the embodiment of the invention shown in FIG. 1 are diagrammed in FIG. 3 for the case of positive ion Electrospray operation from an aqueous solution with proton transfer through semipermeable membrane 2. The same numbers are used to identify the same elements in FIGS. 1 and 3. In the embodiment of the invention diagrammed in FIG. 3, no conductive surfaces are configured in sample solution flow path 3 preventing redox reactions from occurring on surfaces in sample solution flow path 3. Proton charge transfer through cation exchange membrane 2 is diagrammed in FIG. 3 to illustrate proton ion current passing from second solution 58 into the sample solution 57. The total Electrospray current $I_{H1}$ comprising protons and indicated as 61 is equal but opposite in to the electron current $I_{e1}$ indicated as 60 transferred from Membrane assembly electrode 5 into power supply 24. $I_{e1}$ equals the sum of $I_{e2}$, $I_{e3}$ and $I_{14}$ indicated as 62, 63 and 64 respectively. The electron current $I_{e2}$, and $I_{e3}$ and ion current $I_{14}$ is equal to the fraction of the total charge $I_{H1}$ Electrosprayed from tip 8 that impinges on endplate electrode 15 ($I_{e2}$), capillary entrance electrode 23 ($I_{e3}$) or passes into vacuum through capillary orifice 17 ($I_{14}$) respectively. $I_{H1}$ impinges on electrodes 15 and 23 or passes into vacuum as gas phase ions, charged droplets or charged solid aerosols produced in the Electrospray process. Monitoring electron current on electrode elements 5, 15 and 23 during operation provides a means of monitoring and controlling the Electrospray ion current and the pH or cation or anion concentration in sample solution flow channel 3 during Electrospray operation in the embodiment shown in FIG. 3 and other embodiments of the invention described below.

Second solution 58 flowing through second solution flow channel 4 provides a means for running Electrospray current and pH gradients and prevents the depletion of charge which can occur in static reservoirs in electrolytic cells configured and operated with charge removal through semipermeable membranes. It has been found that the flow rate of second solution 58 through second solution flow channel 4 needed to maintain a steady Electrospray current is less than the flow rate of sample solution 57 through sample solution flow channel 3. Depending on the sample solution flow rate and the total Electrospray current run, a minimum second solution flow rate is required to maintain steady and stable conditions. Running the second solution flow rate higher than the minimum required level did not improve performance or change the total ES current. Consequently, running the second solution flow rate just above the minimum required value for a given application greatly reduces second solution consumption during operation. However, operating with higher second solution flow rates through channel 4 allows the running of faster ion current or pH gradients. Second solution flow channel 4 can be configured according to the invention with low dead volume to allow the running of precise and/or rapid gradients with minimum second solution consumption.

Membrane assembly 1 and 40 diagrammed in FIGS. 1 through 3 comprises a flat sheet semipermeable membrane geometry with low dead volume solution flow channels configured on opposite sides of the membrane. Semipermeable membranes 2 or 48 clamped between opposite electrically insulating body elements 65 and 66 can serve as a liquid seal or additional elements 6 can be configured in Membrane assembly 1 to serve as seals to prevent leakage from sample solution 57 or second solution 58, particularly for higher pressure applications. Higher pressures can occur in sample solution flow channel 3 due to sample solution flow through packed or monolithic column 9. As was described above, the pressure gradient across semipermeable membrane 2 can be minimized by including back pressure regulator 27 downstream in second solution flow 4 that references the pressure in sample solution flow channel 3 or by other means known in the art.

Figure 4:
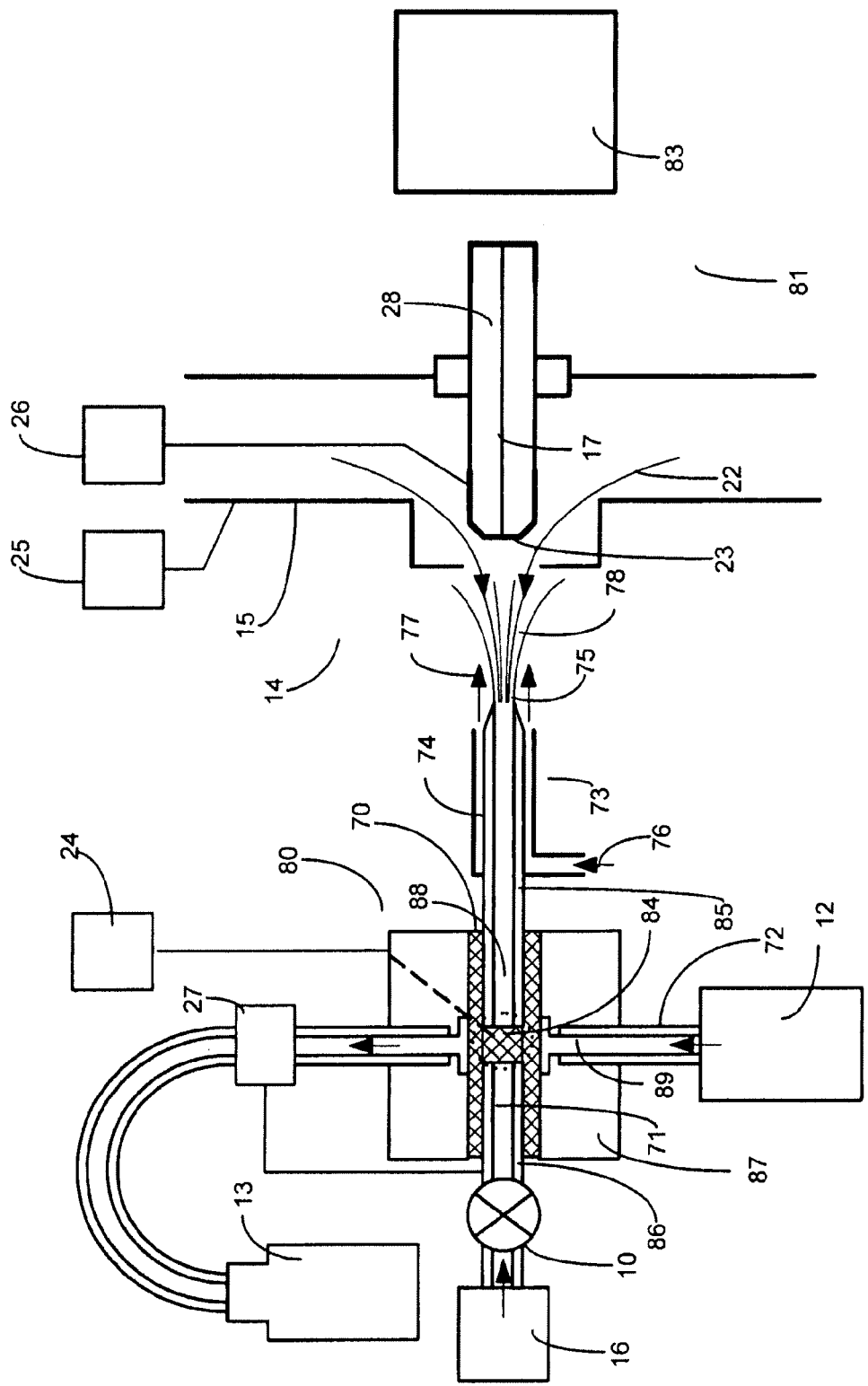
FIG. 4 is a side view cross section diagram of a Membrane assembly comprising a tube shaped semipermeable membrane.
Figure 5:
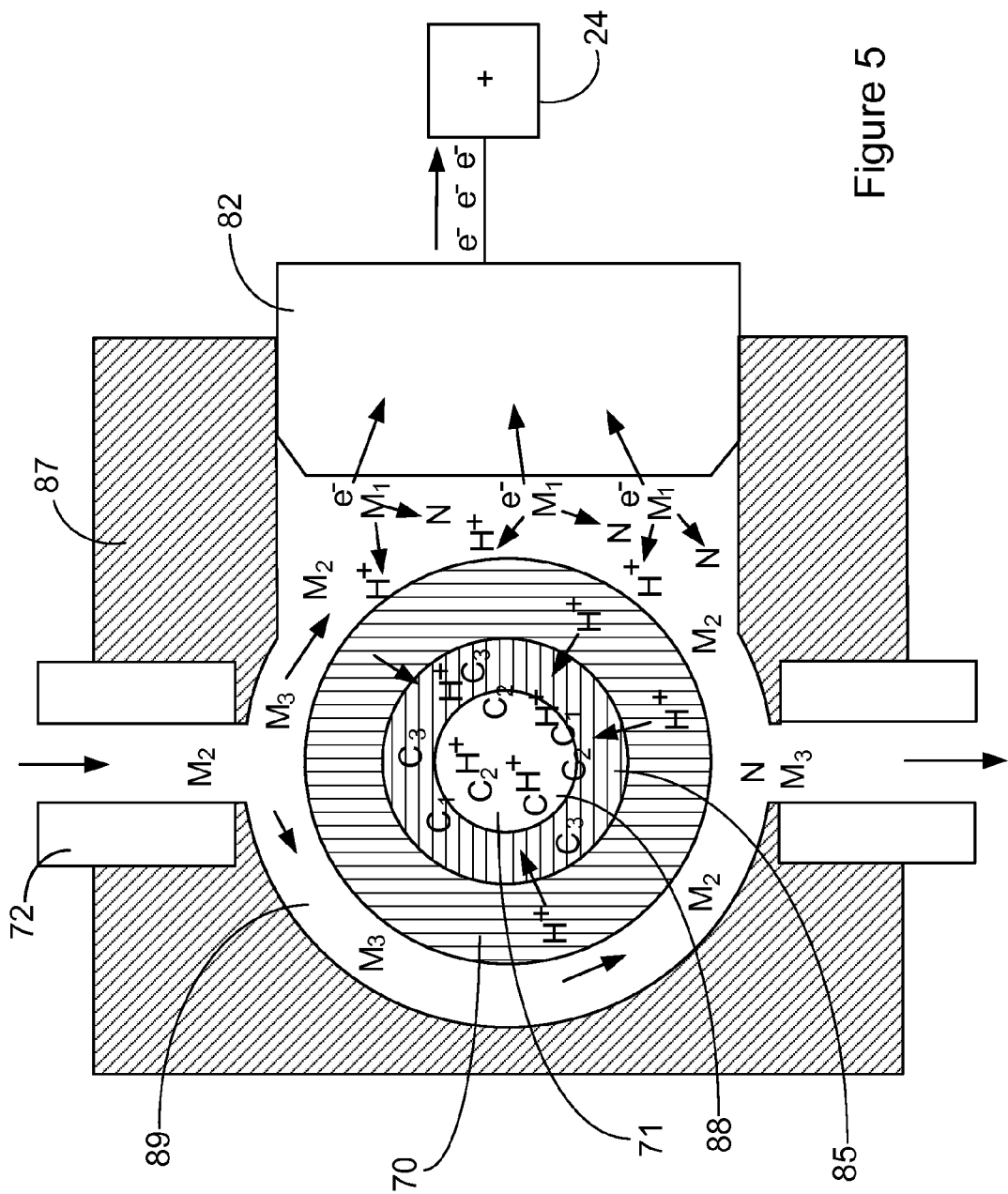
FIG. 5 is a front view cross section diagram of the Membrane assembly shown in FIG. 4.
Figure 6:
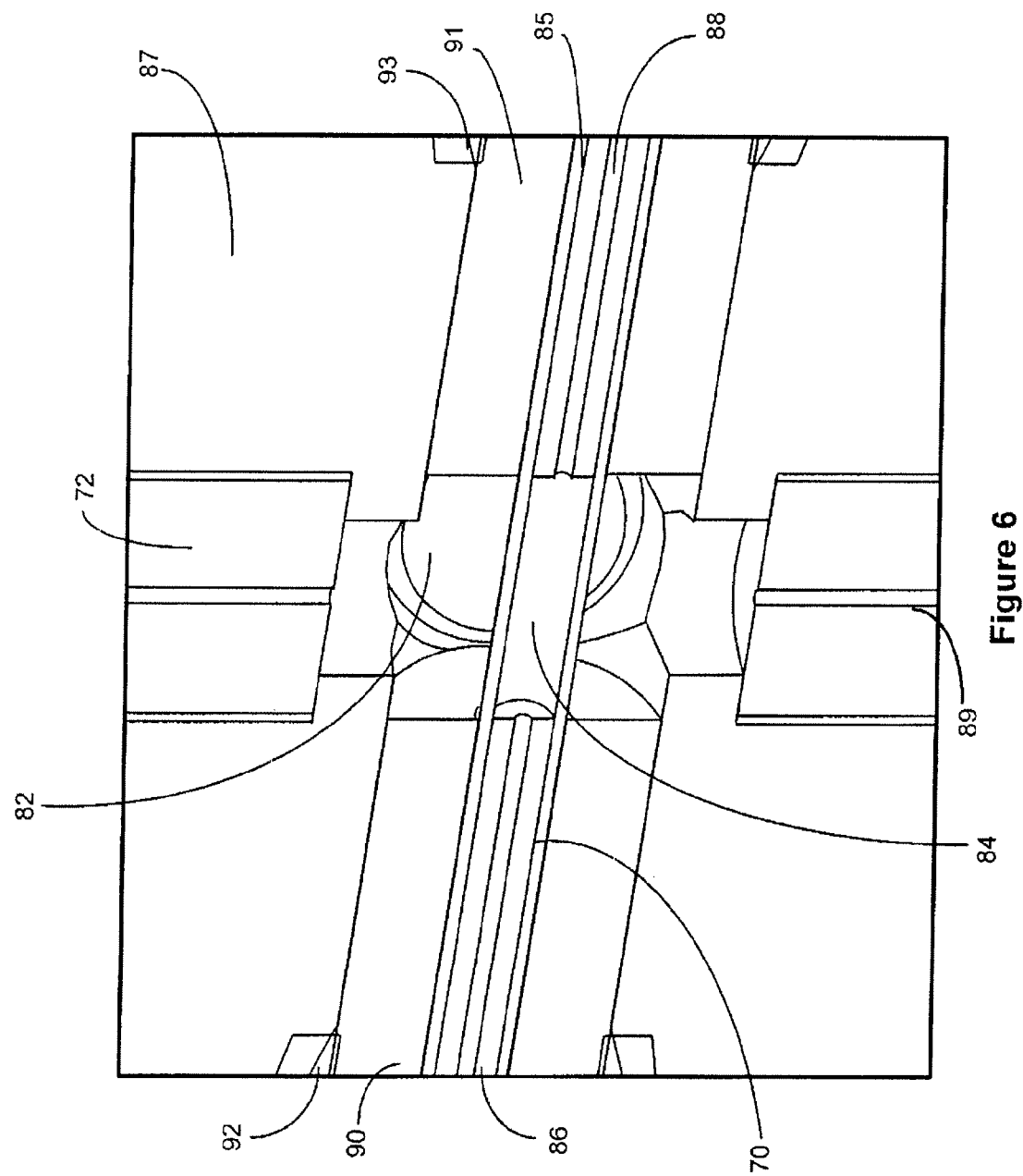
FIG. 6 is a three dimensional angled side view cross section of the Membrane assembly shown in FIG. 4.

An alternative embodiment of the Membrane assembly is diagrammed in FIGS. 4, 5 and 6. FIG. 4 is a cross second side view of Membrane assembly 80 interfaced with Electrospray ion source 14 and mass to charge analyzer and detector 83. FIG. 5 is a cross section front view of Membrane assembly 80 and FIG. 6 is an angle three dimensional cross section view of the center region of Membrane assembly 80. Common elements in FIGS. 4, 5 and 6 share common numbers and element common in to those in FIG. 1 have the same number. Referring to FIGS. 4, 5 and 6, Membrane assembly 80 comprises tube shaped semipermeable membrane 70 and sample solution flow tube sections 85 and 86. As shown in FIG. 6, semipermeable membrane 70 is configured in a sleeve tubes 90 and 91 which form a seal with Membrane assembly body 87 using compression ferrules 92 and 93 respectively. Alternatively semipermeable membrane may be sealed to Membrane assembly body 87 with ferrules compressed directly on semipermeable membrane 70 or semipermeable membrane 70 can be bonded and sealed to Membrane assembly body 87 using an appropriate bonding agent. Gap 84 is configured between sample solution flow tubes 85 and 86 to allow sample solution 88 to contact semipermeable membrane 70 as it flows through Membrane assembly 80. Second solution 89 flows through second solution flow channel 72. Gradient fluid delivery pump 12 provides second solution flow, through Membrane assembly 80 and back pressure regulator 27, into reservoir 13. Gradient fluid delivery pump 12 may be configured as, but is not limited to, a dual syringe pump, dual piston pump, peristaltic pump or a diaphragm pump. Second solution flow channel 72 passes around tube shaped semipermeable membrane 70 in contact with second solution electrode 82. Second solution electrode 82 is connected to dual polarity power supply 24. Sample solution 88 flow is delivered from isocratic or gradient pump or pressurized reservoir 16 through sample injector valve 10, tube 86, gap 84, tube 85 and exits at Electrospray tip 75. Electrospray probe 73 with pneumatic nebulization assist comprises tube 74 with Electrospray tip 75 and nebulizer gas inlet flow 76 and outlet flow 77. Charged droplets formed in Electrospray plume 78 are directed by the Electrospray electric field to move toward the entrance of capillary orifice 17 against heated countercurrent drying gas 22. A portion of the ions formed are swept into vacuum 81 through capillary orifice 17 and are mass to charged analyzed by mass to charge analyzer and detector 83. Vacuum system 81 may comprise one or multiple vacuum stages as is known in the art.

Referencing the embodiment of the invention diagrammed in FIGS. 4, 5 and 6, the surface area of semipermeable membrane 70 in contact with sample solution 88 can be increased or decreased by moving sample solution flow tubes 85 and 86 further apart or closer together respectively. Increasing the semipermeable membrane surface area in contact with sample solution 88 will allow increased ion current capacity required in some applications. The operation of the Membrane assembly shown in FIGS. 4, 5 and 6 is analogous to the flat sheet Membrane assemblies 1 and 40 diagrammed in FIGS. 1, 2 and 3. The voltage difference applied between second solution electrode 82 and end plate electrode 15 and capillary entrance electrode 23 establishes the electric field at Electrospray tip 75. The electric field extends from Electrospray tip 75 through sample solution 88, semipermeable membrane 70 and second solution 89 to second solution electrode 82. The total Electrospray current can be controlled by changing the composition of second solution 89, sample solution 88 or to a limited extent by changing the applied Electrospray voltage but remaining below the onset of corona discharge at Electrospray tip 75. PH scans can be run in sample solution 88 can by ramping or stepping the conductivity of second solution 89. As described above, pH or cation or anion current scans can be run to effect binding, release and/or separation of sample species in RP, NP or IEC packed media in Electrospray needle 74 or in an LC or IEC column configured in sample solution flow path 71 between Membrane assembly 80 and Electrospray probe 73 as diagrammed in FIG. 7.

The sample solution flow path in Membrane assembly 80 and Electrospray probe 73 are configured with no electrically connected conductive surfaces in the sample solution flow path. When injector valve 10 is operated at ground potential during Electrospray operation, the voltage applied to second solution electrode 82 can be adjusted to null any electric field from extending through sample solution flow path 71 upstream of Membrane assembly 80. This prevents any redox reactions from occurring on upstream grounded conductive surfaces in injector valve 10 or fluid pump 16 that are in contact with the sample solution. The elimination of redox reactions occurring on conductive surfaces in the sample solution flow path minimizes or eliminates any redox reaction based changes to sample species and avoids the plating of anion or cation species on upstream surfaces. When the Electrospray ion polarity is switched such plated cation or anion species will reenter the sample solution flow causing unwanted contamination peaks in the mass spectra and potentially compromising Electrospray performance.

Figure 14:
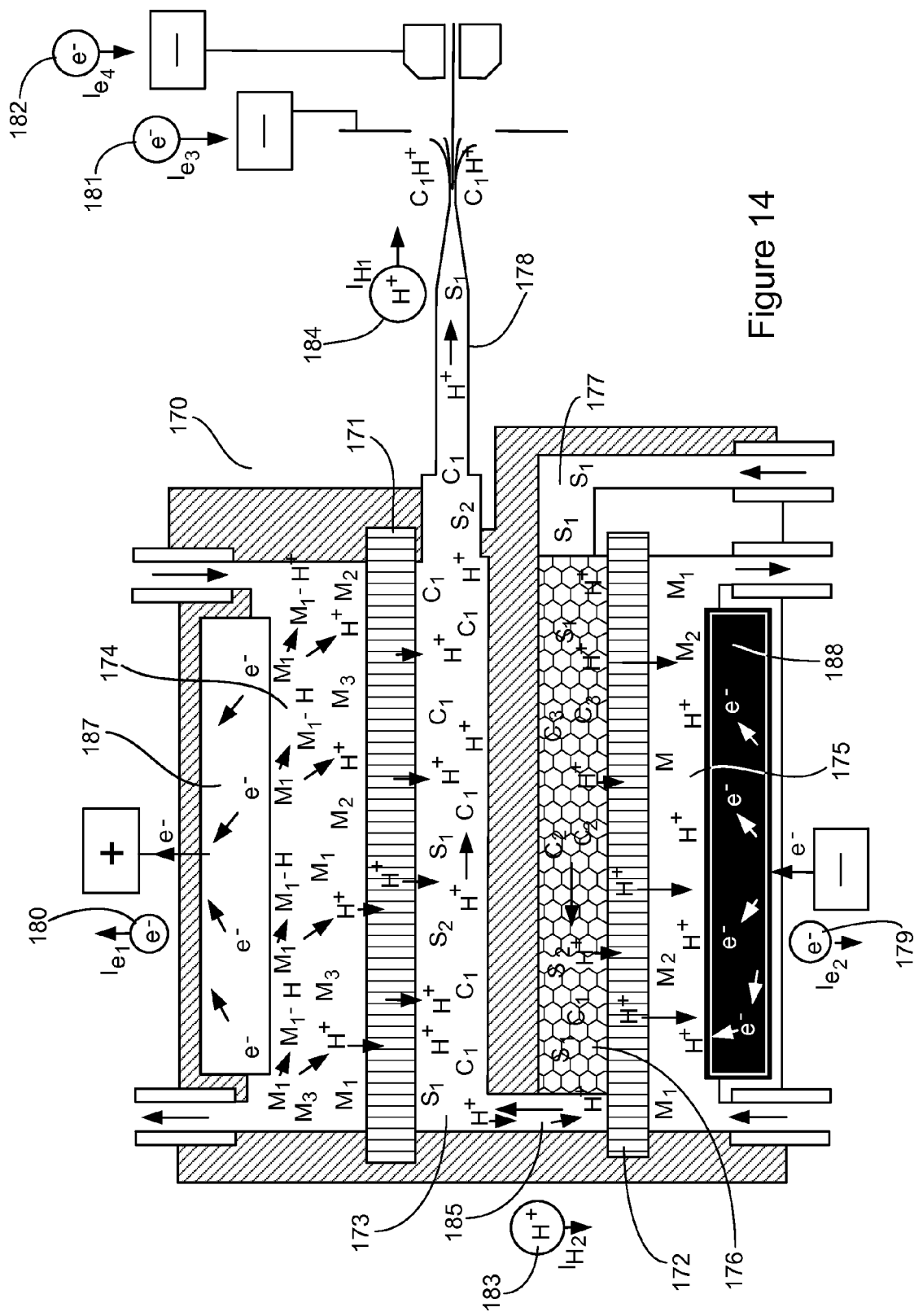
FIG. 14 is a diagram of a two semipermeable membrane assembly with an integrated packed separation column interfaced to an Electrospray inlet probe.

The tube or flat sheet semipermeable membrane configurations are analogous in function but the geometry of one may have an advantage over the other in specific applications. For example, flat sheet semipermeable membranes may be configured with less sample solution channel volume compared with tube shaped semipermeable membrane assemblies. Flat sheet semipermeable membranes provide simpler compact layered flow path geometries as shown in the embodiment of the invention diagrammed in FIG. 14. Tube shaped semipermeable membrane assemblies may provide a geometry advantage when minimum linear contact distance between the sample solution and semipermeable membrane along the solution flow path is desired to effect the highest separation efficiency of sample species. The round tube and flat sheet semipermeable Membrane assembly embodiments shown in FIGS. 1 through 6 can accommodate thicker or thinner semipermeable membranes. Membranes of similar or different material can be stacked or sleeved to improve cation or anion transfer selectivity.

Figure 7:
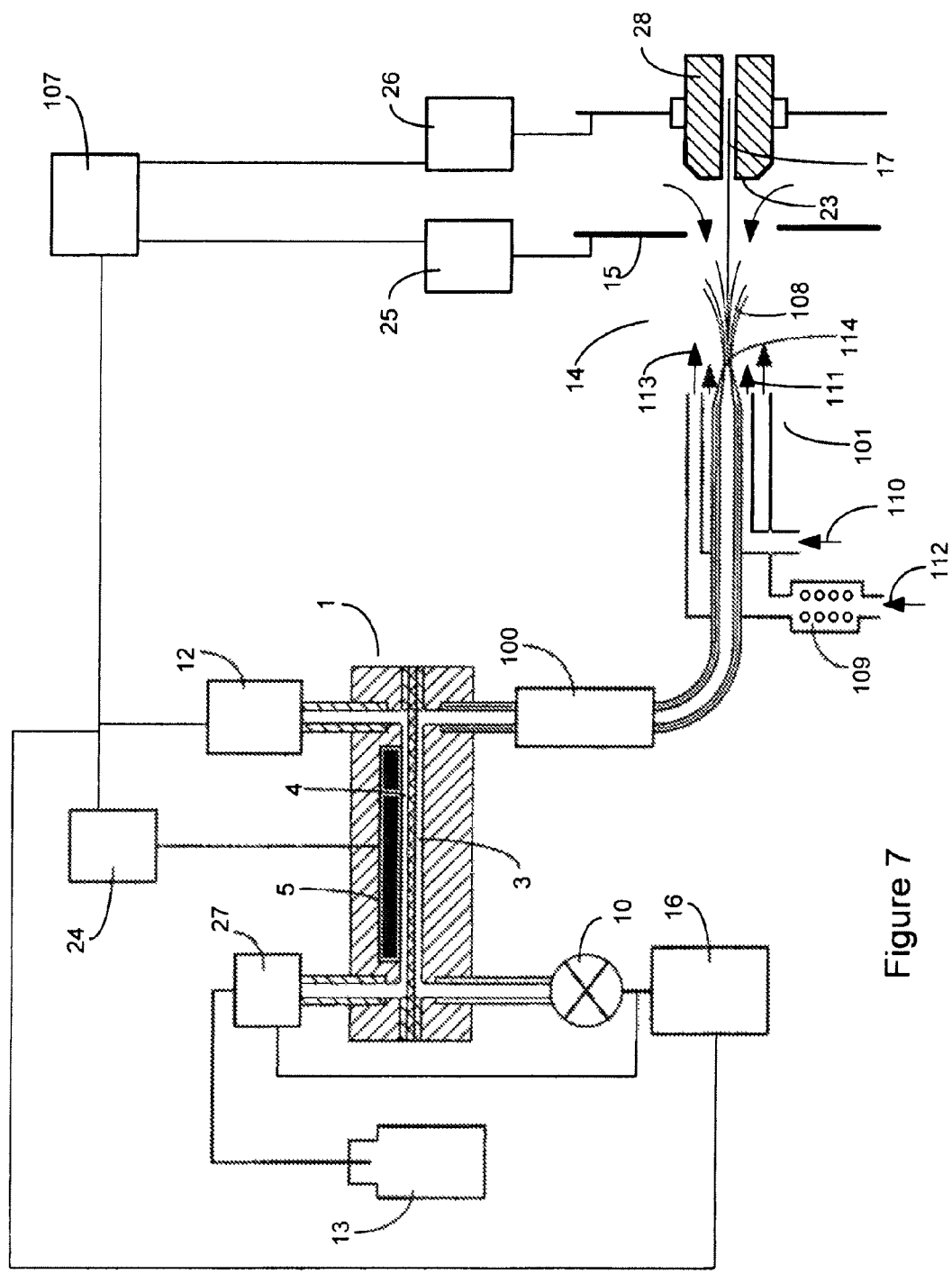
FIG. 7 is a diagram of a packed LC column positioned between an ES inlet probe and a semipermeable Membrane assembly in the sample solution flow path.

An alternate embodiment of the invention is diagrammed in FIG. 7. Similar elements diagrammed in FIGS. 1 and 7 retain the same numbers and function as describe previously. In the embodiment shown in FIG. 7, packed LC or IEC column 100 is configured in sample solution flow path 3 between Membrane assembly 1 and Electrospray probe 101. Packed column 100 is analogous in function to packed column 9 shown in FIG. 1 but allows additional flexibility in accommodating different column sizes, packing materials, column materials, commercial availability and sample solution flow rates. A second heated gas layer is configured in Electrospray probe assembly 101 to facilitate drying of Electrosprayed liquid droplets. Nebulization gas enters Electrospray probe at gas entrance 110 and exits at 111 through an annulus surrounding Electrospray tip 114. Heated gas flow enters the second gas layer at 112 passes through gas heater 109 and exits at 113. Controller 107 connected to power supplies 24, 25 and 26 and fluid delivery systems 12 and 16 can be programmed to provide independent but synchronized control of voltages and sample solution and second solution gradients to optimize sample component cleanup and/or separation and Electrospray performance.

Figure 8:
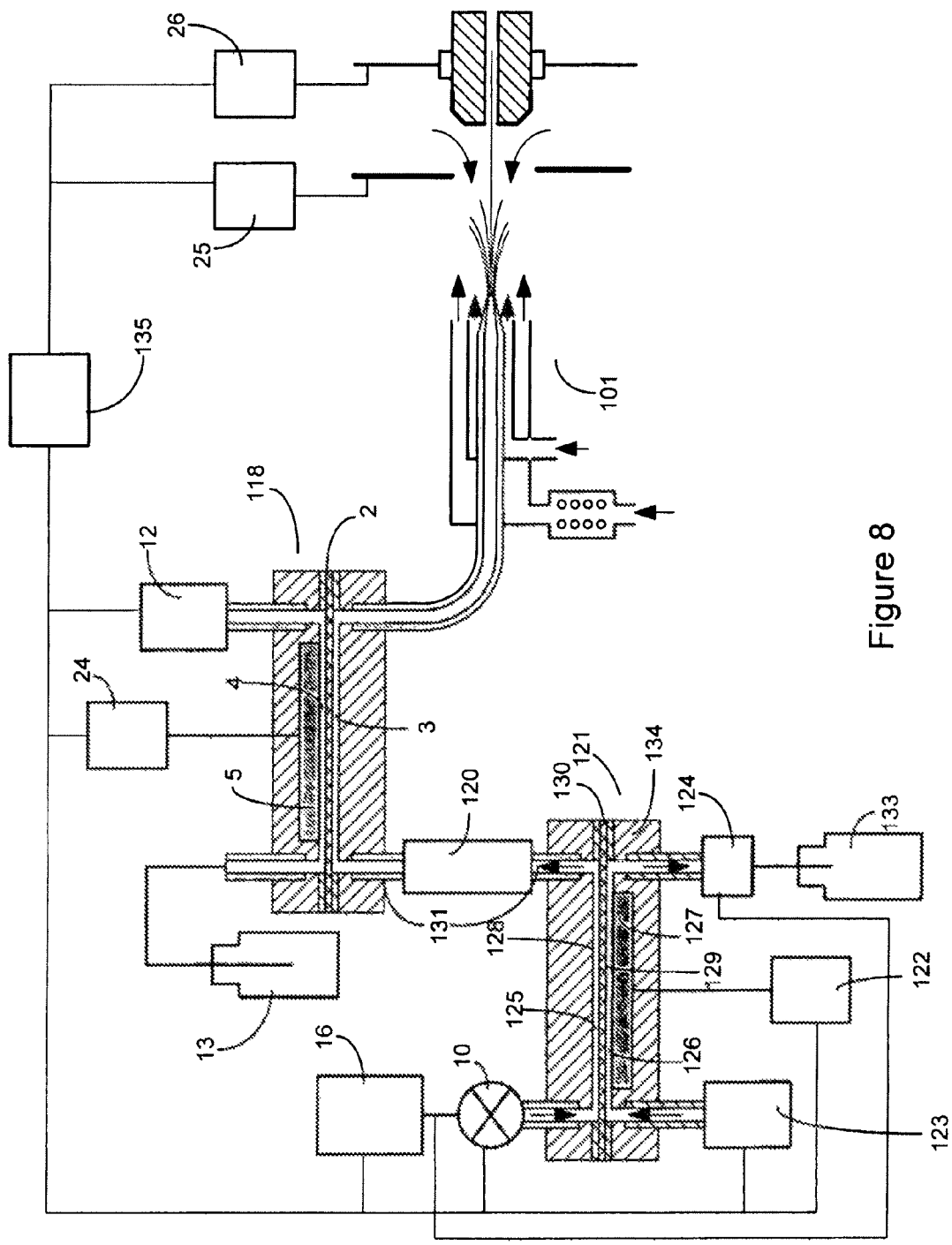
FIG. 8 is a diagram of two semipermeable membrane assemblies positioned upstream and downstream of a packed or open column connected on-line to an Electrospray ion source.
Figure 9:
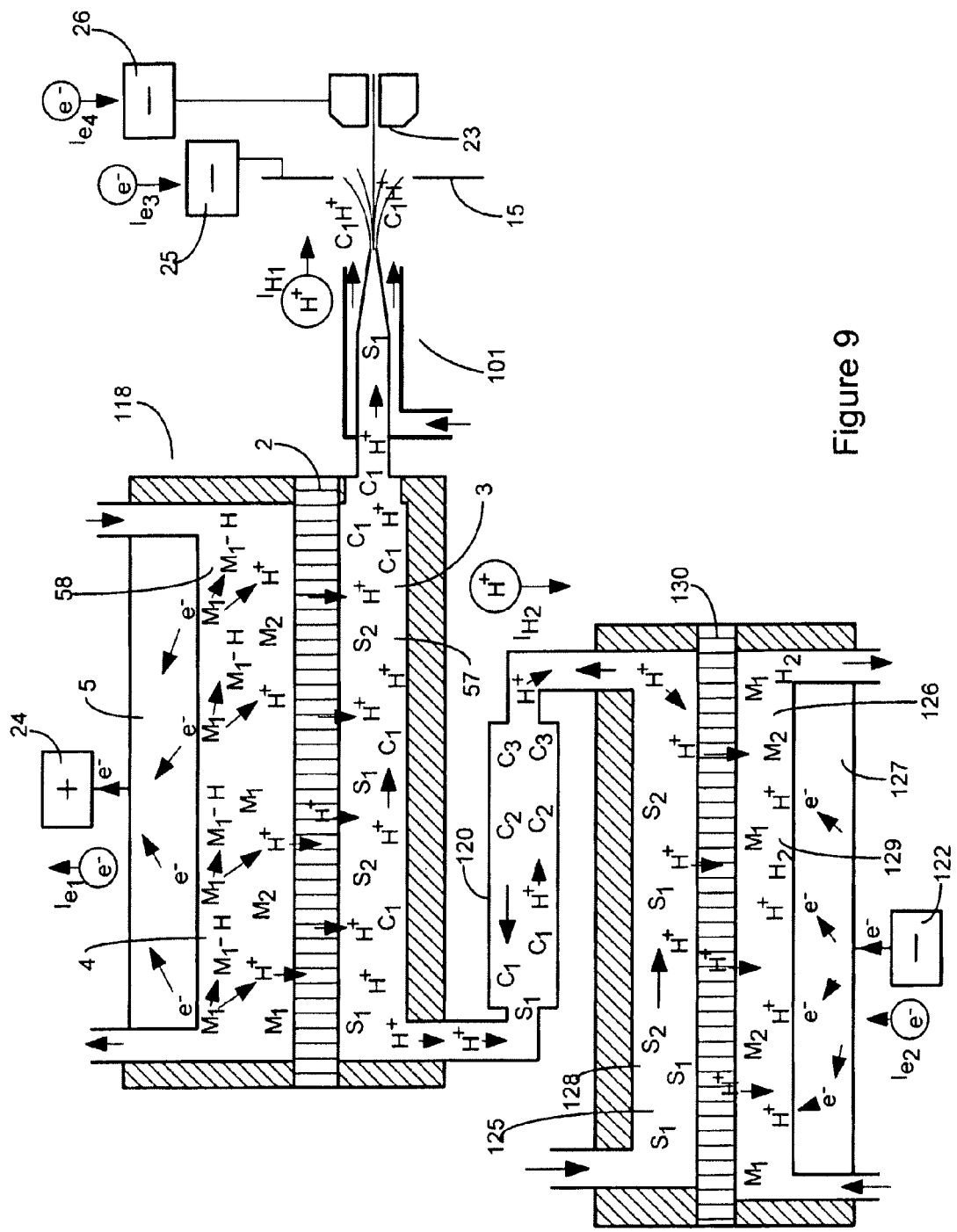
FIG. 9 is a diagram of ion and electrical current passing through the dual semipermeable membrane assembly with sample separation column embodiment shown in FIG. 8.

Two Membrane assemblies are configured in series in an alternative embodiment of the invention diagrammed in FIGS. 8 and 9. Common elements described from alternative embodiments retain the same numbers. Referring to FIGS. 8 and 9, sample solution flow channels 125 and 4 of Membrane assemblies 121 and 118 respectively are configured in series with packed column or open channel 120 positioned in sample solution flow channel 131 connecting sample solution flow channels 125 and 3. Membrane assemblies 121 and 118 can be configured comprising flat sheet semipermeable membranes as diagrammed in FIGS. 1, 2 and 3 or comprising tube shaped semipermeable membranes as diagrammed in FIGS. 4, 5 and 6. Membrane assembly 121 comprises flat sheet or tubular semipermeable membrane 130, sample solution flow channel 125, second solution flow channel 126, second solution electrode 127, dual polarity power supply 122, second solution gradient fluid delivery pump 123, second solution outlet reservoir 133 electrically insulating and chemically inert body 134 and second solution back pressure regulator 124. Similarly Membrane assembly 118 comprises flat sheet or tubular semipermeable membrane 2, sample solution flow channel 3, second solution flow channel 4, second solution electrode 5, second solution outlet reservoir 13, dual polarity power supply 24 and second solution gradient fluid delivery system 12. Membrane assembly 118 sample solution flow channel 3 outlet is interfaced to Electrospray probe 101. Column 120 may be packed with RP, NP or IEC media or may be configured as an open channel column to allow Electrocapture, capture, release or separation functions or capillary electrophoresis separation methods to be run. In the embodiment shown in FIGS. 8 and 9, no electrically conductive surfaces are configured in the sample solution flow path to prevent redox reactions from occurring on conductive surfaces along the sample solution flow path. Elements of sample injection valve 10 and gradient pump 16 that contact the sample solution comprise electrically insulating materials or are electrically floated during operation. All ion current passing through the sample solution flow path and the total Electrospray current must be transferred through semipermeable membranes 134 and 2 during operation.

Adding Membrane assemblies along the sample solution flow path increases the analytical flexibility and capability of LC, IEC, CE and Electrocapture apparatus. Sample species injected into the sample solution flow through sample injection valve 10 enter Membrane assembly 121 as diagrammed in FIG. 9. Relative voltage amplitudes and polarities applied to Membrane assembly 118 second solution electrode 5 and endplate electrode 15 and capillary entrance electrode 23 and the composition of second solution 58 can be adjusted as independent variables to optimize Electrospray and ES MS performance during an analysis as was described above. Upstream sample capture and release steps conducted in column 120, and used for sample concentration, sample cleanup, conducting reactions with sample species and/or separation functions, can be controlled independently of downstream Electrospray operation. Variables used to control functions occurring between the inlet of Membrane assembly 121 and the outlet of Membrane assembly 118 include but are not limited to:

1. The relative voltage polarity and amplitude applied between second solution electrodes 127 and 5,
2. Semipermeable membrane 2 composition (cation or anion exchange membrane),
3. Semipermeable membrane 130 composition (cation or anion exchange membrane),
4. Second solution 58 composition, (isocratic, step function or gradient),
5. Second solution 129 composition, (isocratic, step function or gradient),
6. Column 120 configuration, (packed or open channel),
7. Column 120 packing media, (including but not limited to size exclusion, reverse phase, normal phase or ion exchange chromatography media),
8. Sample solution flow rate, and
9. Sample solution composition, (isocratic, step function or gradient).

The above listed variables can be manually controlled or synchronously controlled through software using controller 135 to conduct one or more of the following analytical functions when a mixture of sample components is injected into sample solution flow 128 through sample injection valve 10:

1. Selective capture and release of sample species on semipermeable membrane 130,
2. Selective capture and release of sample species on the stationary phase of packed column 120 through RP, NP, size exclusion or IEC binding of sample species to the packed media, 3. Selective capture and release of sample species in open channel 120 using Electrocapture,
4. Separation of sample species in open channel 120 using Capillary Electrophoresis,
5. Selective capture and release of sample species on semipermeable membrane 2,
6. Preconcentration, desalting or cleanup of captured samples prior to release of sample species,
7. Reaction of captured sample species with chemical species introduced through injection valve, 10 or through changing sample solution composition delivered by pump 16 through gradients or step functions, and/or
8. Separation of species through controlled release of samples trapped on semipermeable membranes 134 or 2 or in column 120.

FIG. 9 illustrates an example of capture and selective release of sample species in column 120. A mixture of sample components $C_1$, $C_2$ and $C_3$ is injected into sample solution flow 128 through sample injector valve 10. Semipermeable membranes 2 and 130 comprise proton membranes.

Little or no ion current initially passes through column 120 by setting the relative voltages applied to electrodes 127 and 5 to a value that zeros the electron current $I_{e2}$. The sample solution composition is selected to promote binding of sample species on column 120 ion exchange packing material. Bound sample species are then selectively released by increasing the proton current passing between Membrane assemblies 118 and 121. Protons passing through IEC column 120 change the pH to effect sample species release or the protons serve as a cation displacer of bound samples. A pH ramp can be run to effect separation of component species with subsequent on line Electrospray ionization and MS analysis. The proton current amplitude and direction through column 120 can be changed by increasing the relative voltage amplitude and polarity applied to electrodes 5 and 127. The proton current amplitude can also be ramped or stepped by changing the composition of one or both second solutions 58 and 129.

As a second example, column 120 can be configured as an open channel and injected sample components can be Electrocaptured by maintaining an appropriate voltage difference and polarity between electrodes 5 and 127 and controlling the sample solution flow rate. Selective release or separation of Electrocaptured sample components can be achieved by applying one or more of the following methods:
1. Ramping or stepping the composition of one or both second solutions 58 and/or 129 to change the ion current passing through open channel 120.
2. Changing the relative voltage amplitude or polarity applied to electrodes 5 and 127.
3. Change the sample solution flow rate and/or composition.

As a third example, sample components that have a net charge in solution can be trapped at the surface of semipermeable membrane 130 in contact with the sample solution by the applying the appropriate electric field amplitude and polarity. Trapped samples can be concentrated, desalted and subjected to reactions with components added to the sample solution. The relative voltages applied between electrodes 5 and 127 and the composition of second solutions 58 and 129 establish the polarity and amplitude of the electric field at the surface of semipermeable membrane 130. The polarity of this electric field can be reversed as a gradient or step function to release sample components trapped on the surface of semipermeable membrane 130 followed by on-line Electrospray MS analysis.

The relative voltages applied between electrodes 5, 15 and 23 can be held constant to provide consistent Electrospray performance even while changing upstream relative voltages applied between electrodes 5 and 127. Dielectric capillary 28 allows the absolute voltage amplitudes and polarities applied to electrodes 5, 15 and 23 to range over thousands of volts while maintaining the relative voltages and Electrospray performance constant. This allows electrode 129 to be set at or near ground potential to avoid redox reactions from occurring on any electrically connected or grounded conductive surfaces along the sample solution flow path. By maintaining electrode 127 at ground potential, no constraint is placed on upstream component materials and electrical isolation of electrically conductive surfaces is no longer required. Standard commercially available injection valves or pumps can be configured in the embodiment shown in FIGS. 8 and 9. Cation or anion currents passing through packed column or channel 120 can be directly monitored and controlled by measuring electron currents $I_{e2}$ and $I_{e1}$. As described above, the total Electrospray current can be monitored and controlled by measuring electron currents $I_{e1}$, $I_{e3}$ and $I_{e4}$. The total Electrospray current will equal $I_{e1}$ minus $I_{e2}$. The ion current passing through packed column or open channel 120 adds no cation or anion concentration to the sample solution flow exiting Membrane assembly 118. All ion current transferred through one semipermeable membrane that passes through packed column or open channel 120 is removed through the second sample solution by passing through the second semipermeable membrane.

Figure 10:
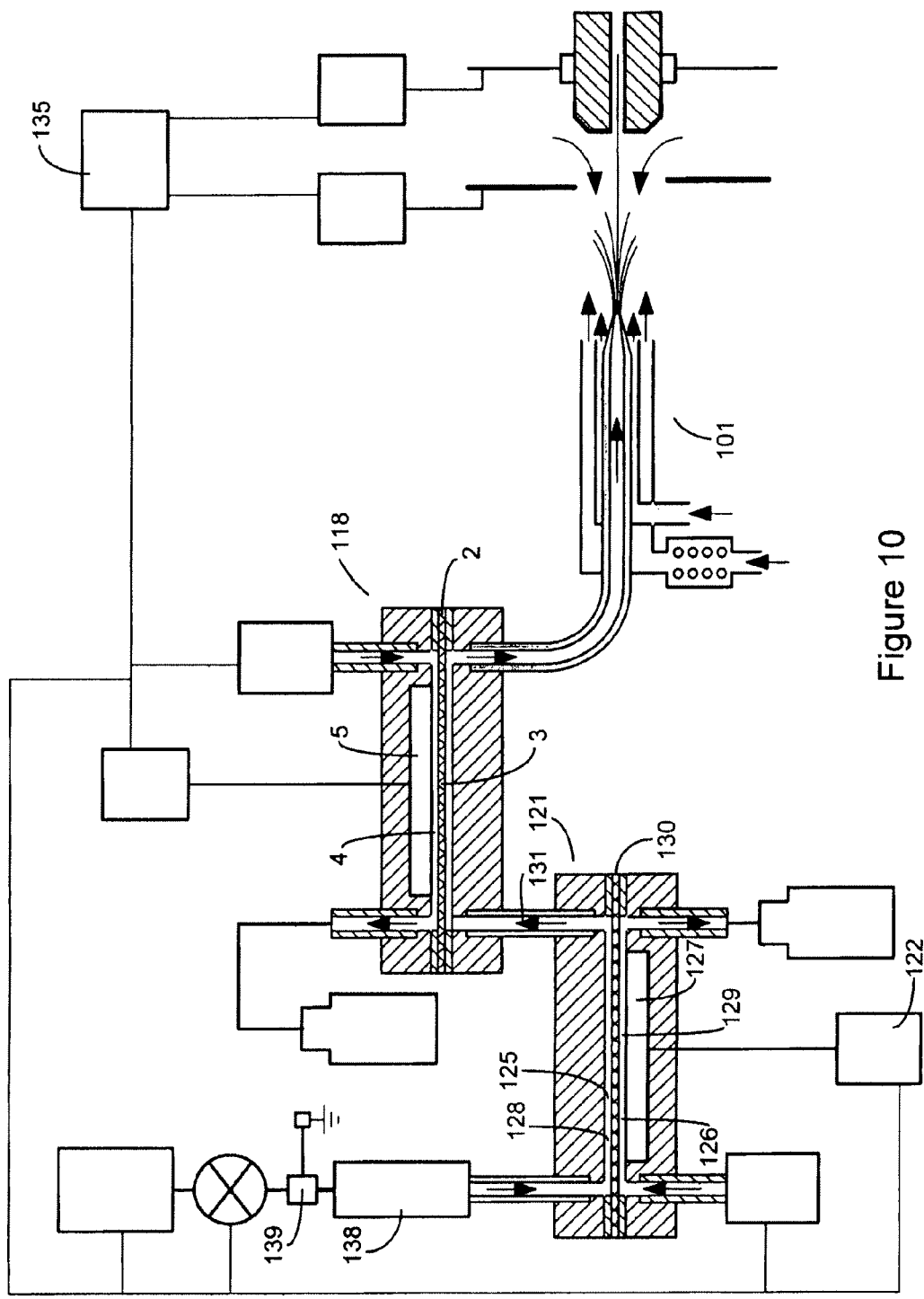
FIG. 10 is a diagram of two semipermeable membrane assemblies configured in series positioned downstream from a packed or open column and upstream from an Electrospray probe in an LC-ES-MS apparatus.

For selected applications, to avoid running a Membrane assembly at higher pressures, packed column or open channel 138 can be configured upstream of Membrane assembly 121 as diagrammed in FIG. 10. Similar elements or assemblies described in alternative embodiments are identified by the same number. Referring to FIG. 10, ion current passing through packed or open channel column 138 is generated at the surface of second solution electrode 127 in Membrane assembly 121 and passes through semipermeable membrane 130. Grounded union or junction 139 completes the ion current circuit from electrode 127. The applied electric field extending through column 138 and the ion current amplitude and direction between grounded union 139 and electrode 127 is controlled by the voltage amplitude and polarity applied to electrode 127, the composition of second solution 129 and the composition of sample solution 128. The relative voltage amplitude and polarity applied between second solution electrodes 5 and 127 can be set to minimize ion current through sample solution flow channel 131. This effectively separates control, composition and polarity of total Electrospray ion current and the ion current passing through column 138. The configuration of ground union 139, however, causes redox reactions to occur on a conductive surface in the sample solution flow channel. By products of such reactions may remain in the sample solution flow path. For example, if sodium cations are transferred though semipermeable membrane 130, are directed through column 138 as ion current and are neutralized on conductive union 139, the neutralized sodium remains in the sample solution flow path which may compromise Electrospray performance. If proton ion current is neutralized on conductive surface 139, hydrogen gas may form in the sample solution flow path which may disrupt downstream processes.

Figure 11:
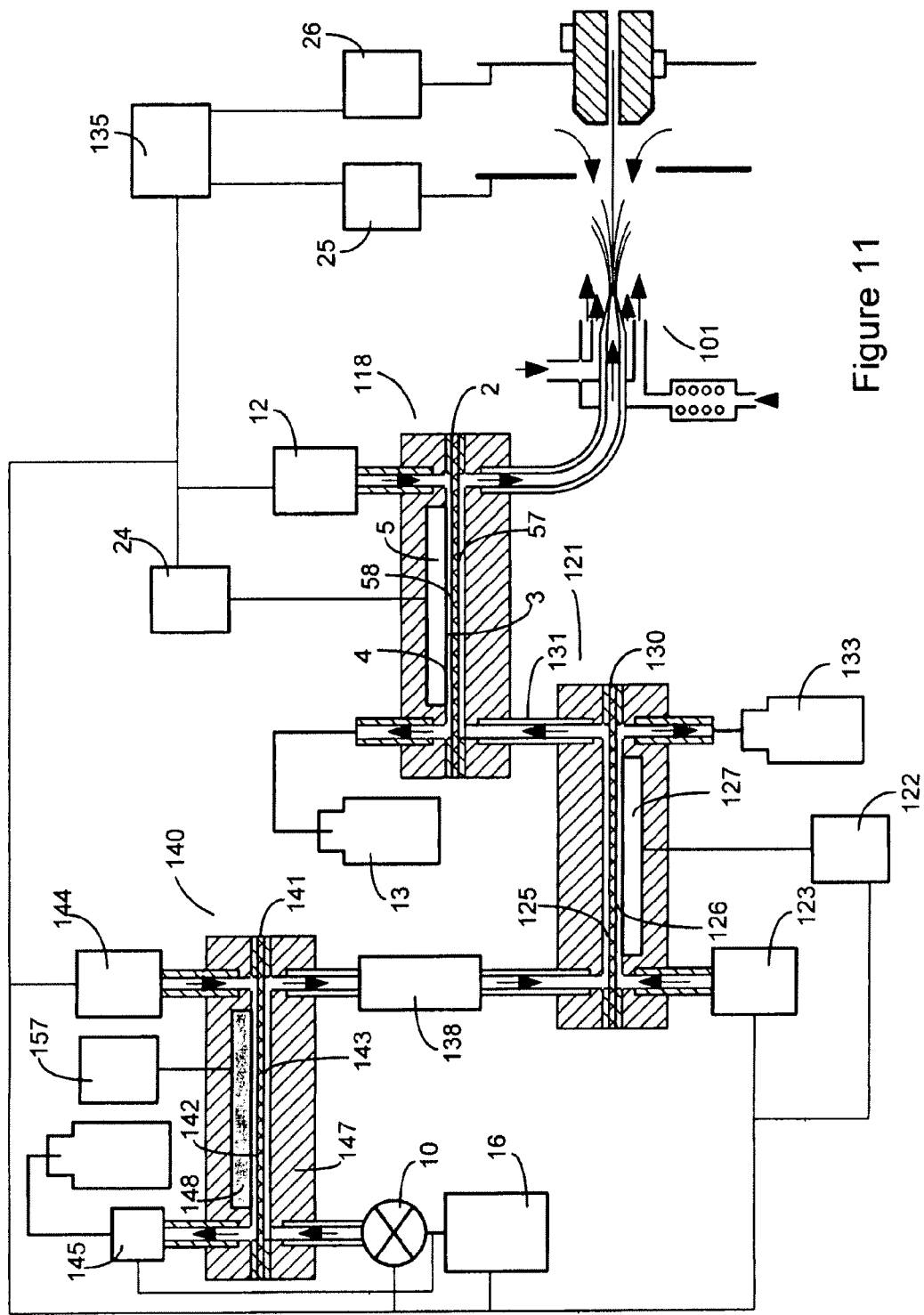
FIG. 11 is a diagram of three semipermeable Membrane assemblies interfaced to an Electrospray inlet probe and configured with a sample separation column positioned between Membrane assemblies two and three.
Figure 12:
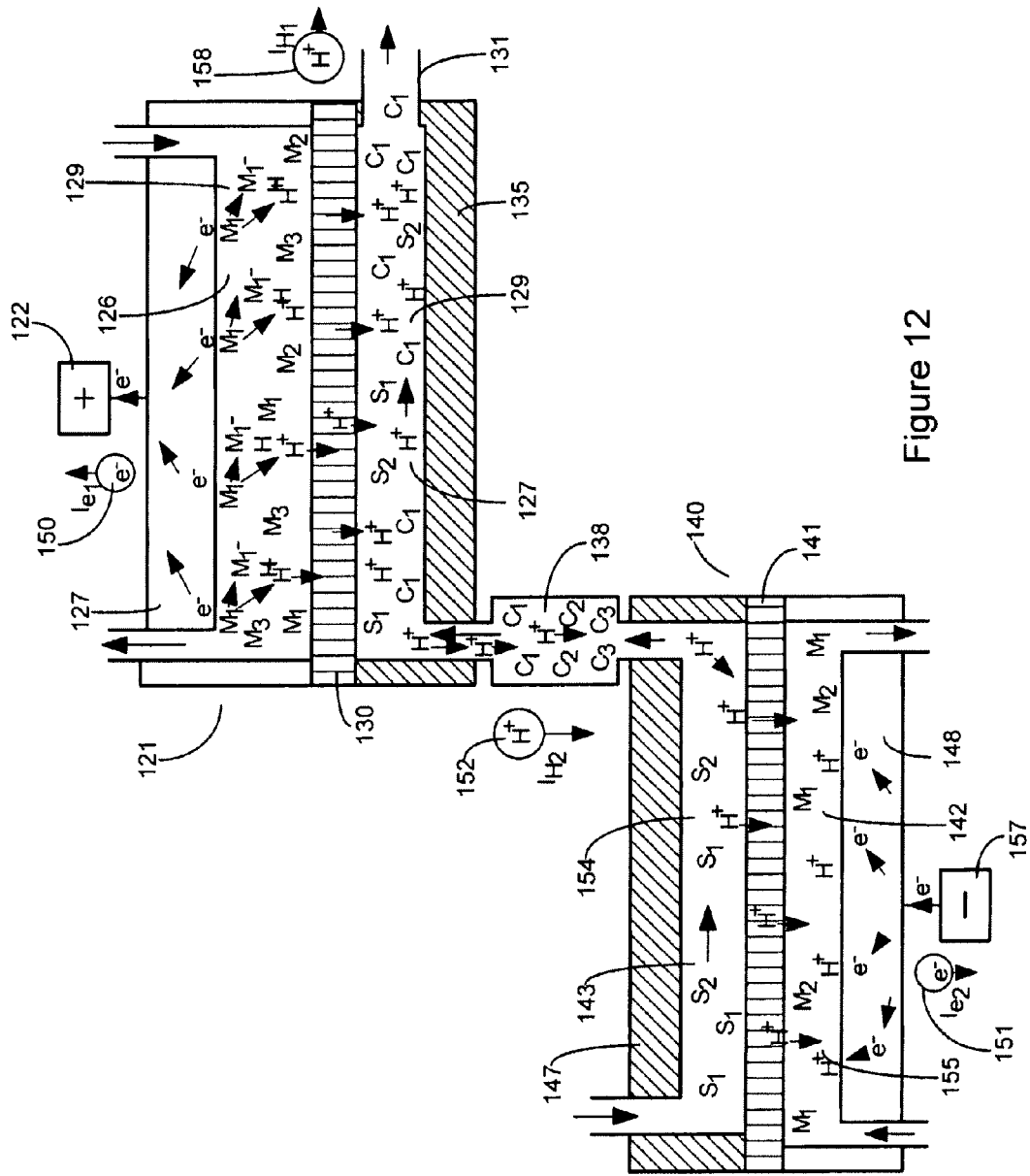
FIG. 12 is a diagram of the ion current passing through upstream Membrane assemblies two and three and the separation column in the embodiment shown in FIG. 11.

To improve analytical performance, capability and flexibility while preventing redox reactions from occurring in the sample solution flow path, three Membrane assemblies can be configured in series along the sample solution flow path as shown in the alternative embodiment of the invention diagrammed in FIGS. 11 and 12. Packed or open Channel column 138 is positioned upstream in the sample solution flow path from Membrane assemblies 121, 118 and Electrospray probe 101. Sample injected through sample injection valve 10 flows though Membrane assembly 140 sample solution flow channel 143, packed column or open channel 138, Membrane assembly 121 sample solution flow channel 125, connecting channel 131, Membrane assembly 118 sample solution flow channel 3 and is Electrosprayed from Electrospray probe 101 with subsequent mass to charge analysis and detection. Similar to two Membrane assembly embodiments, back pressure regulator 145 referencing the pressure in sample solution flow channel 143 minimizes the pressure differential across semipermeable membrane 141 configured in Membrane assembly 140. Dual polarity power supply 157 supplies voltage to second solution electrode 148 and gradient pump 144 delivers second solution flow with isocratic or varying composition to second solution flow channel 142.

The three Membrane assembly embodiment diagrammed in FIG. 11 allows independent control of the upstream sample component capture, release and separation functions and the downstream the Electrospray process. FIG. 12 shows an example operating mode where protons are generated through oxidation reactions occurring at the surface of second solution electrode 127 and are transferred through cation exchange membrane 130 into sample solution flow channel 127. Proton ion current passes through packed column or open channel 138 driven by the electric field maintained between second solution electrodes 127 and 148 in Membrane assemblies 121 and 140 respectively. Protons then pass through cation exchange membrane 141 and are reduced on second solution electrode 148 configured in Membrane assembly 140.

The relative voltage amplitude and polarity applied to second solution electrodes 5 and 127 can be controlled to minimize or prevent upstream ion current from passing through sample solution flow channel 131. Alternatively, the composition, amplitude and direction of ion current passing through sample solution flow channel 131 can be controlled by using one or more of the following variables:
1. The relative voltage polarity and amplitude applied between second solution electrodes 127 and 5,
2. Semipermeable membrane 2 composition (cation or anion exchange membrane),
3. Semipermeable membrane 130 composition (cation or anion exchange membrane),
4. Second solution 58 composition, (isocratic, step function or gradient),
5. Second solution 129 composition, (isocratic, step function or gradient)
6. Sample solution flow rate, and
7. Sample solution composition, (isocratic, step function or gradient).

As described above for the two Membrane assembly embodiment shown in FIG. 8, Electrocapture sample component preconcentration, capture, release and separation methods can be run in sample solution flow channel 131 by controlling the electric field and ion current amplitude and direction and the sample solution flow rate in sample solution flow channel 131. Depending on the application requirements, one ion species of anions or cations can be generated and directed through packed column or open channel 138 and a different ion species of anions or cations can be generated to pass through sample solution flow channel 131. Ion current directed through pack column or open channel 138 and sample solution flow channel 131 can be controlled to have:
1. The same or different amplitude,
2. The same or different direction,
3. The same or different cation or anion generation source,
4. The same or different cation or anion species, or
5. The same or different ion polarity.

Each of the above conditions can remain static or be changed during a run. Ion current composition, amplitude and direction through packed column or open channel 138 can be controlled using one or more of the following variables:
1. The relative voltage polarity and amplitude applied between second solution electrodes 127 and 148,
2. Semipermeable membrane 130 composition (cation or anion exchange membrane),
3. Semipermeable membrane 141 composition (cation or anion exchange membrane),
4. Second solution 129 composition, (isocratic, step function or gradient),
5. Second solution 155 composition, (isocratic, step function or gradient),
6. Column 138 configuration, (packed or open channel),
7. Column 138 packing media, (including but not limited to size exclusion, reverse phase, normal phase or ion exchange chromatography media),
8. Sample solution flow rate, and
9. Sample solution composition, (isocratic, step function or gradient).

The voltage amplitude and polarity applied to second solution electrode 148 can be set close to ground potential to prevent redox reactions from occurring on upstream conductive surfaces. All other downstream and Electrospray source electrodes can be adjusted to optimize desired sample component preconcentration, desalting, cleanup, separation or reactions with reagent species functions and Electrospray ionization mass analysis performance.

The above listed variables can be manually controlled or synchronously controlled through software using controller 135 to conduct one or more of the following analytical functions when a mixture of sample components is injected into the sample solution flow through sample injection valve 10:
1. Selective capture and release of sample species on semipermeable membrane 148,
2. Selective capture and release of sample species on semipermeable membrane 130,
3. Selective capture and release of sample species on semipermeable membrane 2,
4. Selective capture and release of sample species on the stationary phase of packed column 138 through RP, NP, size exclusion or IEC binding of sample species to the packed media,
5. Selective capture and release of sample species in open channel 138 using Electrocapture,
6. Selective capture and release of sample species in open channel 131 using Electrocapture,
7. Preconcentration, desalting or cleanup of captured samples prior to release of sample species in packed column or open channel 138 or open channel 131,
8. Reaction of captured sample components with reagent chemical species introduced through injection valve 10 or through changing sample solution composition delivered by pump 16 through gradients or step functions in packed column or open channel 138 or open channel 131, and/or
9. Separation of species through controlled release of samples trapped on semipermeable membranes 141, 130 and/or 2, in column or open channel 138 or in open channel 131.

Electron currents 150 and 151 can be monitored to control the ion current 152 through packed column or open channel 138 or ion current 158 through open channel 131. All ion current passing through packed column or open channel 138 can be removed from the sample flow solution before the sample flow solution passes through open channel 131 by controlling electron currents 150 and 151 to be equal but opposite in direction and zeroing ion current 158 using methods described above. For example sodium cations can be used to displace sample species from ion exchange media packed in column 138 and removed from the sample flow solution upstream of Membrane assembly 2 as sodium ion current would reduce Electrospray performance. Simultaneously and independently, protons can be generated in Membrane assembly 118 to provide the Electrospray ion current. Specifically in this example, a sodium cation current is generated at the surface of electrode 148 in second solution 155 of Membrane assembly 140 and directed through semipermeable membrane 141 configured as a cation exchange membrane. Driven by the electric field maintained along the sample solution flow path by voltages applied to second solution electrodes 148 and 127, the sodium cation current passes through packed column 138 displacing sample species captured on the ion exchange media packed in column 138. After exiting column 138, excess sodium cations are removed from the sample solution flow, by passing through semipermeable membrane 130 configured as a cation exchange membrane, driven by the electric field, and reduced or neutralized at the surface of second solution electrode 127. Protons are independently generated at the surface of second solution electrode 5 through oxidation reactions driven by the Electrospray electric field and are transferred through semipermeable membrane 2 configured as a cation exchange membrane to provide the Electrospray current. Multidimensional preconcentration, cleaning, and separations of sample species can be performed by synchronizing the capture, release and separation functions conducted in packed column or open channel 138 and those conducted in open channel 131.

Figure 13:
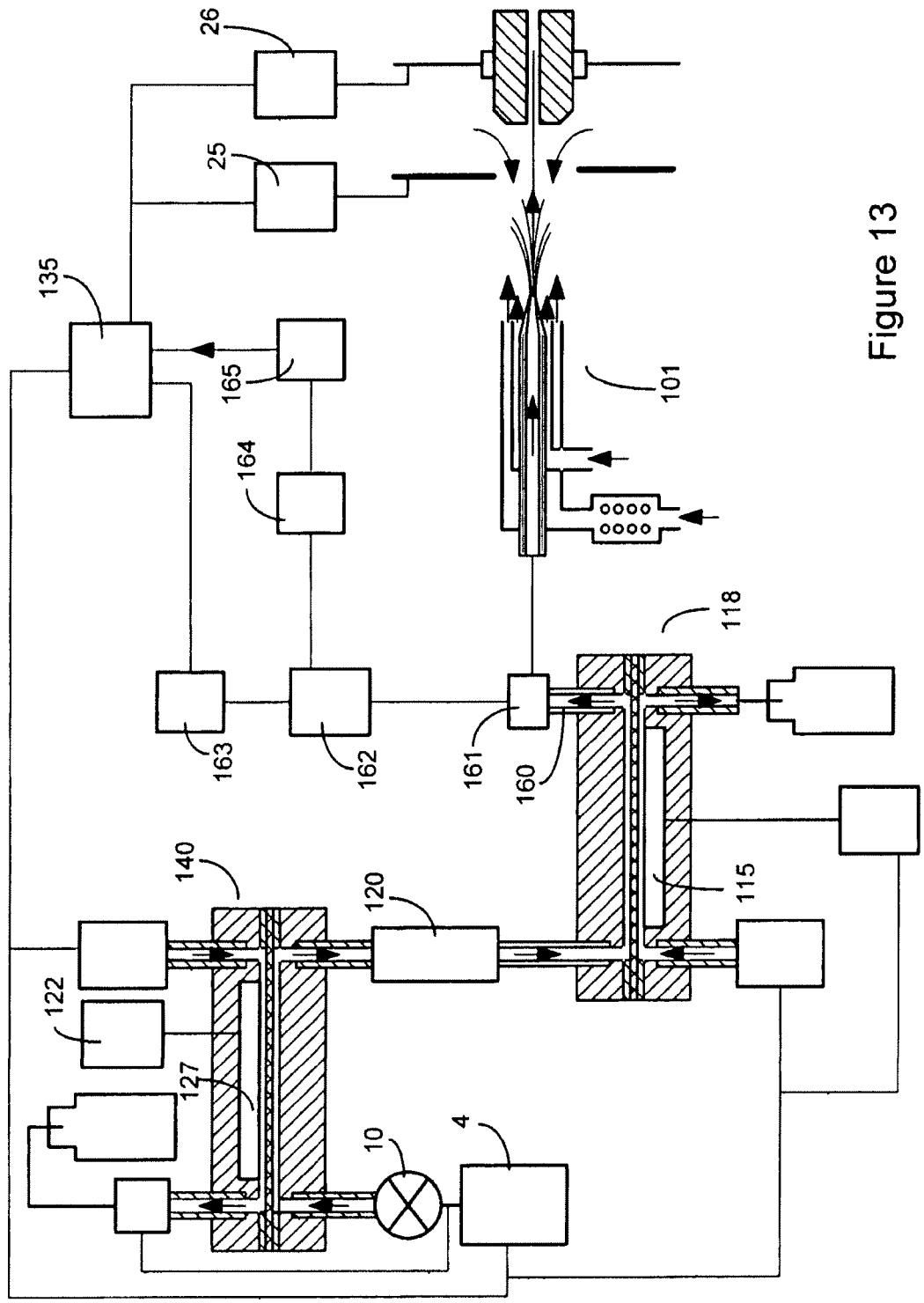
FIG. 13 is a diagram of two semipermeable membrane assemblies configured with a separation column, an Electrospray ion source and a light absorption detector.

All operating modes of the three Membrane assembly embodiment of the invention can be controlled manually or synchronously through software control through controller 135. Different detectors can be used to detect sample components exiting Membrane assembly 118 as diagrammed in FIG. 13. Separation of sample species in packed column or open channel 120 has been described above. Separated sample components exit Membrane assembly 118 carried by the sample solution flow through channel 160. In the embodiment of the invention diagrammed in FIG. 13, the sample solution flow is split in flow splitter 161 with a portion of sample solution flow directed though Electrospray inlet probe 101 with the remainder directed through UV detector flow cell 162. Sample solution passes through UV detector flow cell 162 and is fraction collected in fraction collector 163. UV detector electronics 164 and logic interface 165 send the digitized UV detector signal to controller 135. The sample solution flow path through UV detector flow cell 162 and fraction collector 163 is electrically isolated to avoid redox reactions from occurring in the sample solution flow path due to any Electrospray electric field. UV detector 162 can be any type of detector used in LC, IEC, CE or CEC including but not limited to variable or multiple wavelength light adsorption detectors (photodiode arrays), conductivity detectors or condensation nuclei particle counting detectors. Other mass spectrometer ion sources including but not limited to Atmospheric Pressure Chemical Ionization (APCI), Photoionization, Inductively Coupled Plasma (ICP), or combination Electrospray and APCI sources can be used instead of Electrospray ion sources interfaced to mass spectrometers.

In an alternative embodiment of the invention, one or more Membrane assemblies, packed columns and/or open channels can be configured in a single integrated assembly. Integrated assemblies can be configured to minimize size and sample solution flow channel dead volumes and flow rates. An integrated two Membrane assembly embodiment of the invention is diagrammed in FIG. 14 wherein packing or monolithic sample separation media 176 is configured in the sample solution flow path 177 in contact with semipermeable membrane 172. Dual Membrane assembly 170 comprises downstream semipermeable membrane 171, sample solution flow channel 173, second solution flow channel 174 and second solution electrode 187 and upstream semipermeable membrane 172, sample solution flow channel 177, second solution flow channel 175 and second solution electrode 188. Solution flow channel 173 is integrated into Electrospray probe 178 whereby no conductive surfaces are configured in the sample solution flow path to prevent redox reactions from occurring in the sample solution flow path. Dual Membrane assembly 170 can be run in operating modes similar to those described for the two Membrane assembly embodiment of the invention diagrammed in FIG. 8. Open channel 185 can be run in Electrocapture and release mode as a compliment or in series with chromatography functions run using packed or monolithic media 176. Efficient and rapid displacement of selected components trapped on media 176 can be achieved, to effect separation of sample components, due to the close proximity and contact of media 176 to semipermeable membrane 172. Ions passing through semipermeable membrane 172 are in contact with a large portion of the packing or monolithic separation media 176 so tightly controlled ion currents can provide a nearly uniform chemical environment throughout the volume of packing or monolithic material 172. Ion currents 183 passing through sample solution flow channel 185 and the total Electrospray current 184 can be controlled by monitoring electrical currents 179, 180, 181 and 182 and controlling voltages applied to electrodes, second solution composition, sample solution composition and flow rate, semipermeable membrane materials and packing or monolithic separation media composition as has been described for alternative embodiments above. Dual membrane assembly 170 can be readily scaled up or down in size and alternatively configured with tubular instead of flat sheet semipermeable membrane elements. Additional semipermeable membrane layers can be added to an integrated assembly to increase analytical functional capability, performance and flexibility.

Figure 15:
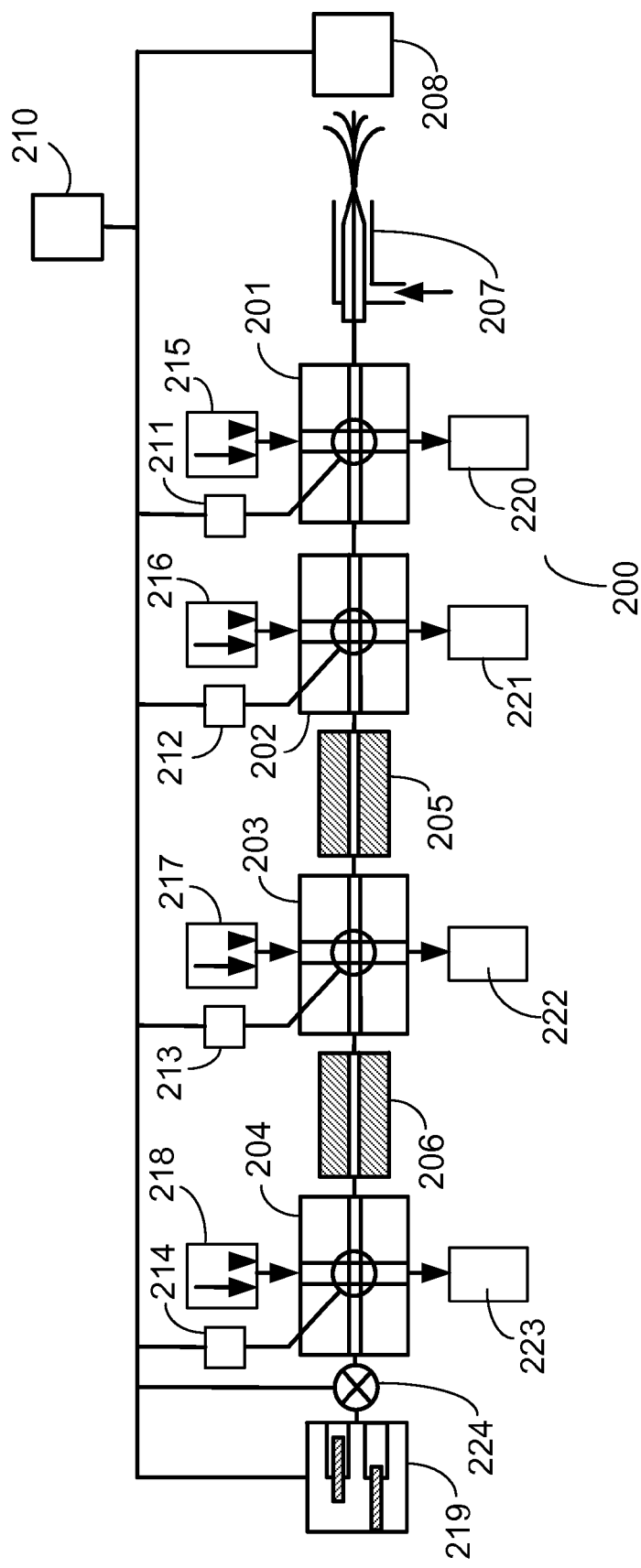
FIG. 15 is a diagram of a three semipermeable membrane assembly comprising two open separation columns interfaced to an Electrospray inlet probe.
Figure 16:
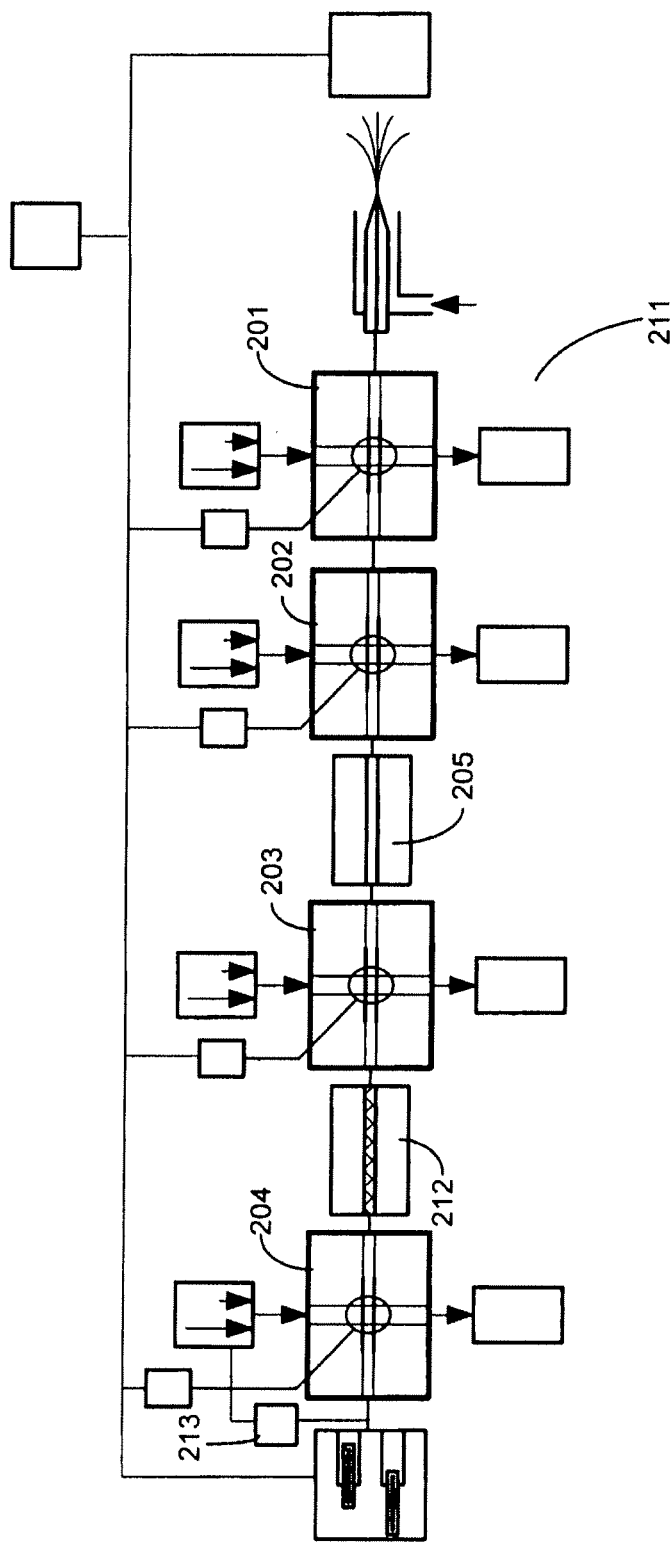
FIG. 16 is a diagram of a three semipermeable membrane assembly comprising one packed and one open separation column interfaced to an Electrospray inlet probe.

FIG. 15 shows a diagram of a four Membrane assembly embodiment of the invention that can be configured with discrete components and assemblies or as one integrated assembly. Four Membrane assembly apparatus 200 comprises Membrane assemblies 201, 202, 203 and 204 with second solution gradient pumps 215, 216, 217 and 218 respectively and second solution outlet reservoirs 220, 221, 222 and 223 respectively. Sample solution is delivered using gradient pump 219 and sample is injected through sample injection valve 224. The four Membrane assembly apparatus is interfaced to Electrospray probe 207 and mass spectrometer 208 with all functions synchronized and controlled through controller 210. Two open channel sections 205 and 206 are sequentially positioned along the sample solution flow path between Membrane assemblies 221 and 222 and 222 and 223 respectively. The four Membrane assembly embodiment diagrammed in FIG. 15 allows multidimensional trapping, release and separation analytical functions as described above conducted online with Electrospray mass spectrometric analysis. An extended range of analytical methods can be programmed and controlled in a modular fashion using controller 210. Components can be swapped out or added to rapidly reconfigure system as diagrammed in FIG. 16 wherein a packed chromatography column 212 replaces open channel section 206 in four Membrane assembly apparatus 211. Back pressure regulator 213 is added to minimize any pressure gradient across the semipermeable membrane configured in Membrane assembly 204. Using the embodiment of the invention diagrammed in FIG. 16, orthogonal sample preconcentration, reaction, cleaning and/or separations can be performed through the packed RP, NP, IEC or CEC column 212 and open channel 205.

Alternative embodiments of Membrane assemblies and combinations of Membrane assemblies, ion sources, detectors and analyzers can be configured, including but not limited to parallel Membrane assembly configurations and using gas phase ion mobility detectors or ion mobility detectors interfaced to mass spectrometers. Although the present invention has been described in accordance with the embodiments shown, one of ordinary skill in the art will recognized that there can be variations to the embodiments, and those variations would be within the spirit and scope of the present invention.

It should be understood that the preferred embodiment was described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly legally and equitably entitled.

We claim:

1. An apparatus for analyzing chemical species comprising:
   a. at least one membrane assembly each comprising a semipermeable membrane, a first flow channel having a first flow channel inlet and a first flow channel outlet, a second flow channel having a second flow channel inlet and a second flow channel outlet, said semipermeable membrane separating said first and said second flow channels, and an electrode positioned in said second flow channel,
   b. during operation of the apparatus, a first and a second solution flow in said first and said second flow channels, respectively,
   c. means for regulating a pressure gradient across said semipermeable membrane between said first and said second flow channels of said at least one membrane assembly;
   d. means for introducing sample species into said first solution,
   e. a detector responsive to at least a portion of said sample species flowing from said first flow channel outlet of said at least one membrane assembly, and
   f. at least one means for capturing, releasing, or separating said portion of said sample species in said first solution, said means connected to said first solution flow.

2. The apparatus according to claim 1 wherein said detector comprises an ion source for producing gas-phase ions of said portion of said sample, a mass analyzer for mass-to-charge analyzing said ions, and a mass analyzer detector for detecting said mass-to-charge analyzed ions.

3. The apparatus according to claim 1 wherein said means for capturing, releasing, or separating comprises a chromatography column.

4. The apparatus according to claim 1 wherein said means for capturing, releasing, or separating comprises an electrocapture open channel.

5. The apparatus according to claim 1, wherein said ion source comprises an electrospray ion source.

6. The apparatus according to claim 1 wherein said apparatus comprises a means for applying and controlling voltages applied to said electrode.

7. The apparatus according to claim 1 wherein said apparatus comprises means for independently changing a composition of at least one of said first and said second solutions.

8. The apparatus according to claim 1 wherein said semipermeable membrane comprises a cation exchange membrane.

9. The apparatus according to claim 1 wherein said semipermeable membrane comprises an anion exchange membrane.

10. The apparatus according to claim 1 wherein said detector comprises a light absorption detector.

11. The apparatus of claim 2, wherein said means for capturing, releasing, or separating said portion of said sample species in said first solution comprises a packed chromatography column connected to said first flow channel.

12. A method for analyzing chemical species comprising:
   a. utilizing the apparatus of claim 11,
   b. flowing a first solution and a second solution in said first and said second flow channels, respectively,
   c. injecting sample species into said first flow channel,
   d. regulating the pressure gradient across said semipermeable membrane between said first and said second flow channels,
   d. generating at least one ion current in said second flow channel and directing said ion current through said semipermeable membrane into said first solution flow,
   f. controlling an amplitude and a direction of said at least one ion current in said first flow channel,
   g. using said ion current to capture said sample species on or release said sample species from said packed chromatography column,
   h. directing said at least one ion current to said electrospray ion source for electrospray ionization of said released sample species, and
   i. mass to charge analyzing said ionized sample species in said mass analyzer.

13. The apparatus of claim 2, wherein said means for capturing, releasing, or separating said portion of said sample species in said first solution comprises an electrically insulated open channel connected to said first flow channel.

14. A method for analyzing chemical species comprising:
   a. utilizing the apparatus of claim 13,
   b. flowing a first solution and a second solution in said first and said second flow channels,
   c. injecting sample species into said first flow channel,
   d. regulating the pressure gradient across said semipermeable membrane between said first and said second flow channels,
   e. generating at least one ion current in said second flow channel and directing said ion current through said semipermeable membrane into said first solution flow,
   f. controlling an amplitude and a direction of said at least one ion current in said first flow channel,
   g. using said ion current to capture, release, and/or separate said sample species,
   h. directing said at least one ion current to said electrospray ion source for electrospray ionization of said separated sample species and
   i. mass to charge analyzing said ionized sample species in said mass analyzer.

15. The apparatus of claim 1, wherein said means for capturing, releasing, or separating at least a portion of said sample species in said first solution comprises an electrically insulated open channel connected to said first flow channel.

16. A method for analyzing chemical species comprising:
   a. utilizing an the apparatus of claim 15,
   b. flowing a first solution and a second solution in said first and said second flow channels,
   c. injecting sample species into said first flow channel,
   d. regulating the pressure gradient across said semipermeable membrane between said first and said second flow channels,
   e. generating at least one ion current in said second flow channel and directing said ion current through said semipermeable membrane into said first solution flow,
   f. controlling an amplitude or direction of said at least one ion current in said first flow channel,
   g. using said ion current to capture, release, and/or separate said sample species in said open channel, and
   h. detecting said released sample species with said detector.

17. A method for analyzing chemical species comprising:
   a. utilizing an the apparatus of claim 15,
   b. flowing a first solution and a second solution in said first and said second flow channels,
   c. injecting sample species into said first flow channel,
   d. regulating the pressure gradient across said semipermeable membrane between said first and said second flow channels,
   e. generating at least one ion current in at least one said second flow channel and directing said ion current through said semipermeable membrane into said first solution flow,
   f. controlling an amplitude and a direction of said at least one ion current in said first flow channel,
   g. using said ion current to capture said sample species on or release said sample species from said semipermeable membrane, and
   h. detecting said released sample species with said detector.

18. A method according to claim 12 wherein said release of said sample species is controlled to effect separation of said sample species.

19. A method according to claim 12 wherein said controlling said at least one ion current comprises changing a composition of said second solution.

20. A method according to claim 12 wherein said controlling said at least one ion current comprises changing a voltage applied to said electrode.

21. A method according to claim 16 wherein said detector is a light absorption detector.

22. A method according to claim 12 wherein said packed chromatography column is an ion exchange chromatography column and said release of said ion species is conducted using ion exchange.

23. A method according to claim 12 wherein at least one said semipermeable membrane is a cation exchange membrane.

24. A method according to claim 12 wherein at least one said semipermeable membrane is an anion exchange membrane.

25. A method according to claim 12 wherein said controlling said at least one ion current amplitude comprises gradually or abruptly changing a pH in a portion of said first flow channel.

26. A method according to claim 12 wherein a portion of said ion current directed into said first flow channel through said semipermeable membrane is removed from said first flow channel through a different semipermeable membrane.

27. A method according to claim 17 wherein electrocapture is used to effect said capture, release, and separation of said sample species.

28. A method according to claim 14 wherein capillary electrophoresis is used to effect said separation of said sample species.

* * * * *

UNITED STATES PATENT AND TRADEMARK OFFICE
CERTIFICATE OF CORRECTION

PATENT NO. : 8,487,243 B2
APPLICATION NO. : 13/006934
DATED : July 16, 2013
INVENTOR(S) : Craig M. Whitehouse and Thomas P. White It is certified that error appears in the above-identified patent and that said Letters Patent is hereby corrected as shown below:

In the Claims:

In column 27, line 4, claim 16, delete "an the" and insert -- the --,

In column 27, line 21, claim 17, delete "an the" and insert -- the --.

Signed and Sealed this
Twenty-second Day of October, 2013

Teresa Stanek Rea
*Deputy Director of the United States Patent and Trademark Office*